US006956650B2

(12) United States Patent
Boas et al.

(10) Patent No.: US 6,956,650 B2
(45) Date of Patent: Oct. 18, 2005

(54) SYSTEM AND METHOD FOR ENABLING SIMULTANEOUS CALIBRATION AND IMAGING OF A MEDIUM

(75) Inventors: David A. Boas, New Market, NH (US); Joe Culver, Salem, MA (US); Simon Arridge, London (GB); Thomas Gaudette, Jamaica Plain, MA (US)

(73) Assignee: General Hospital Corporation, Boston, MA (US)

( * ) Notice: Subject to any disclaimer, the term of this patent is extended or adjusted under 35 U.S.C. 154(b) by 369 days.

(21) Appl. No.: 10/045,309

(22) Filed: Jan. 10, 2002

(65) Prior Publication Data

US 2003/0030809 A1 Feb. 13, 2003

Related U.S. Application Data

(60) Provisional application No. 60/261,492, filed on Jan. 12, 2001.

(51) Int. Cl.[7] .......................... G01N 21/59; G01N 21/49
(52) U.S. Cl. ........................... 356/432; 356/39; 600/473
(58) Field of Search .................... 356/39, 432; 600/310, 600/473, 476, 477

(56) References Cited

U.S. PATENT DOCUMENTS 6,516,209 B2 * 2/2003 Cheng et al. ............... 600/473

FOREIGN PATENT DOCUMENTS

| EP | 0627620 | 6/2004 |
| WO | WO 9852646 | 11/1998 |
| WO | WO 0119241 | 3/2001 |

* cited by examiner

Primary Examiner—Richard A. Rosenberger
(74) Attorney, Agent, or Firm—Dorsey & Whitney LLP

(57) ABSTRACT

The methods and systems are provided that alleviate the impact of experimental systematic errors. These calibration methods and systems can be based on the discovery that by including source and detector calibration factors as part of the inverse calculation for image reconstruction, image artifacts can be significantly reduced. The novel methods and systems enhance contrast in images of the distribution of the radioactive properties of a medium, and enable improved detection of, for example, spatial variations in optical properties within highly scattering media, such as human or animal tissue. The novel methods and systems receive radiation which exits from the medium. Then, one or more optical properties of the medium are derived using the received radiation and one or more calibration factors, wherein the calibration factors are variables. Subsequently, a distribution of the optical properties in the medium is determined using the derived optical properties.

137 Claims, 20 Drawing Sheets

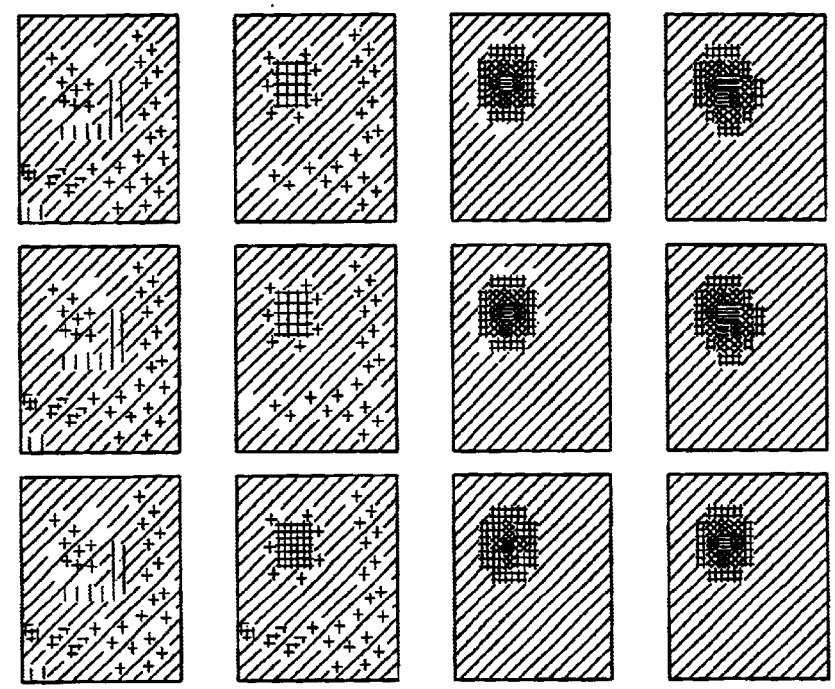
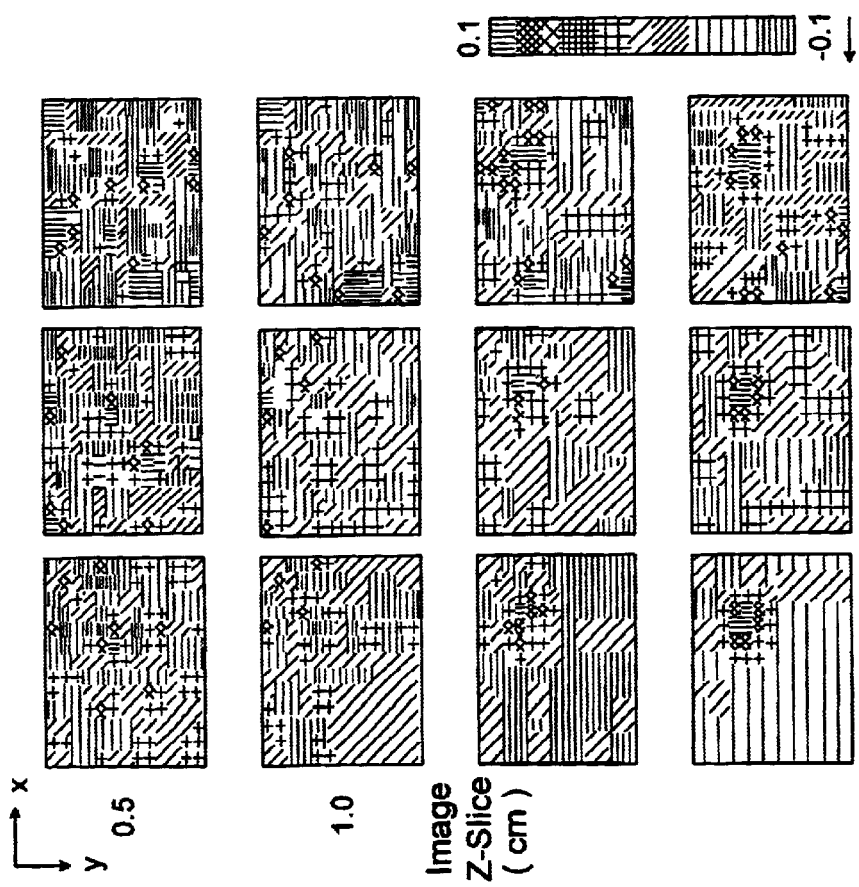

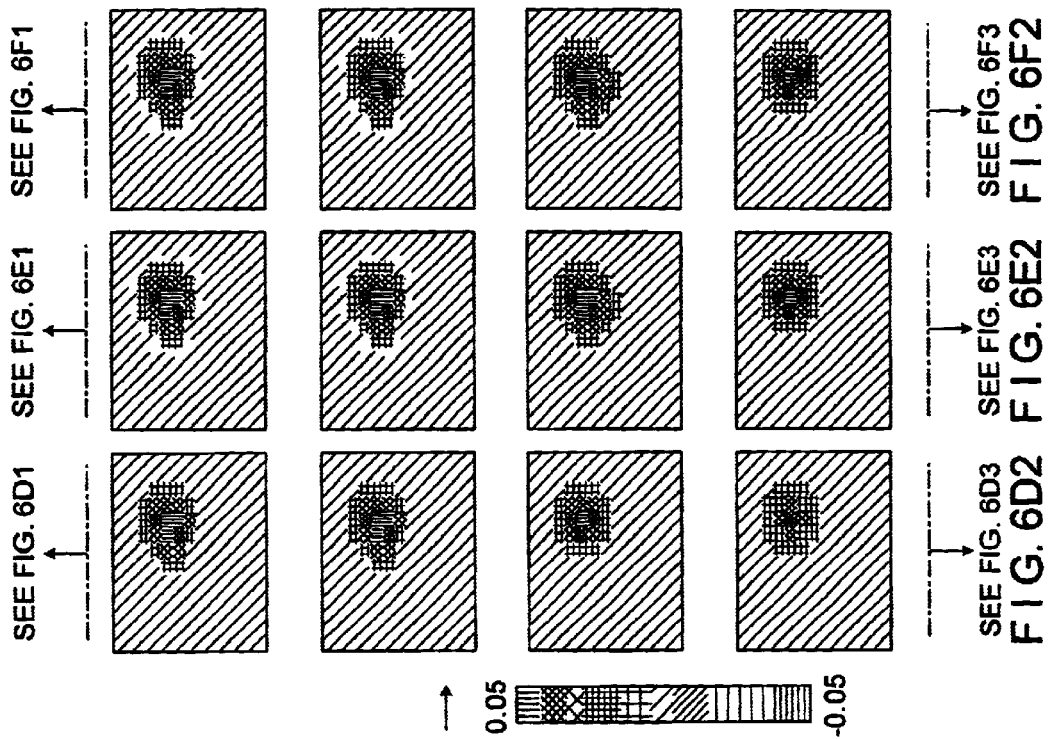
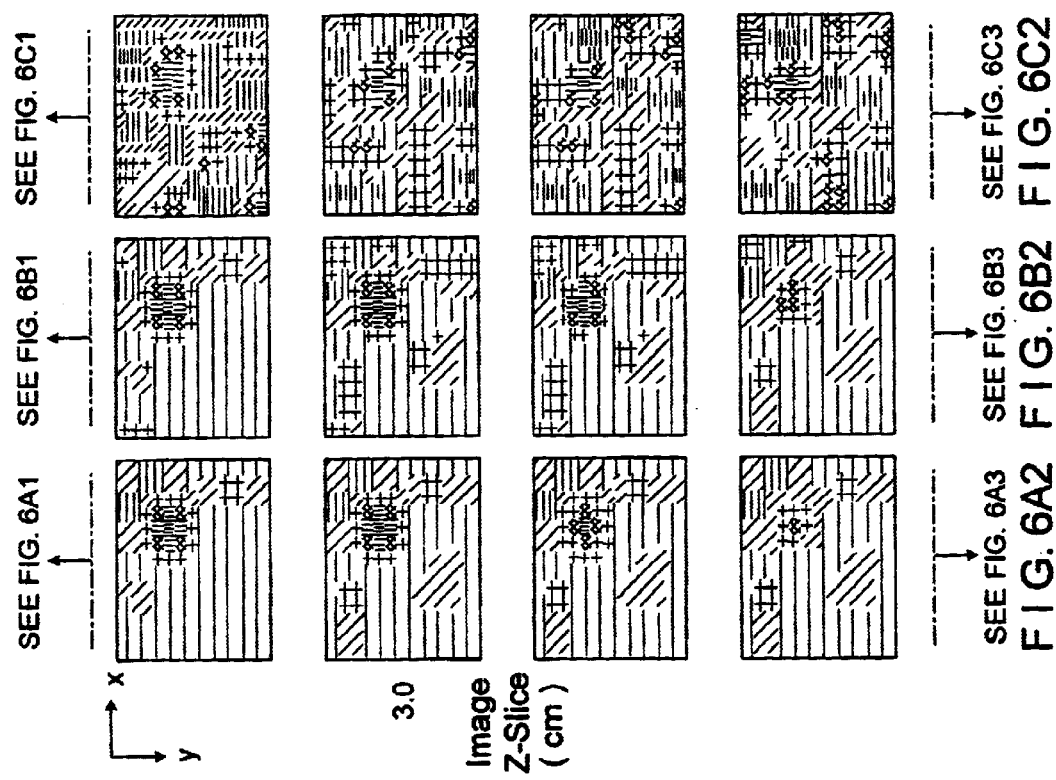

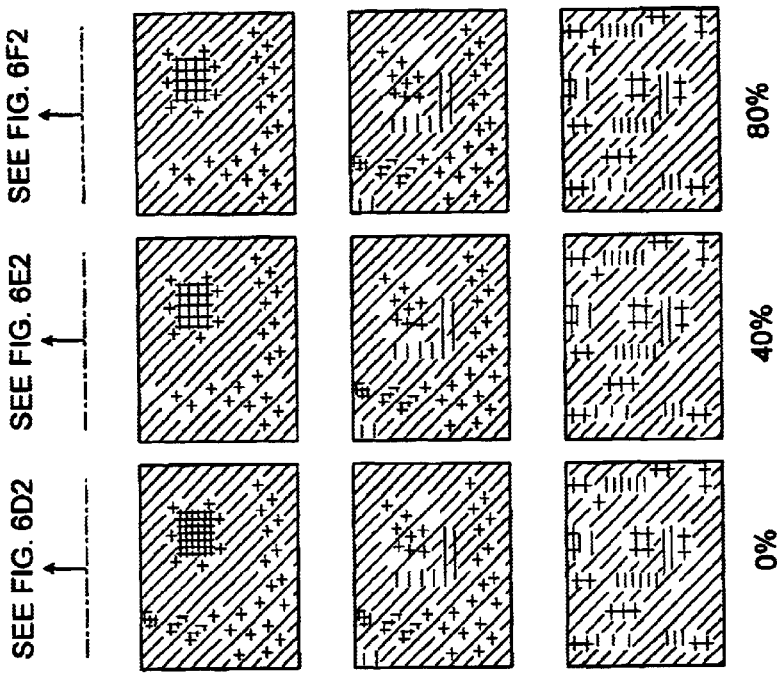
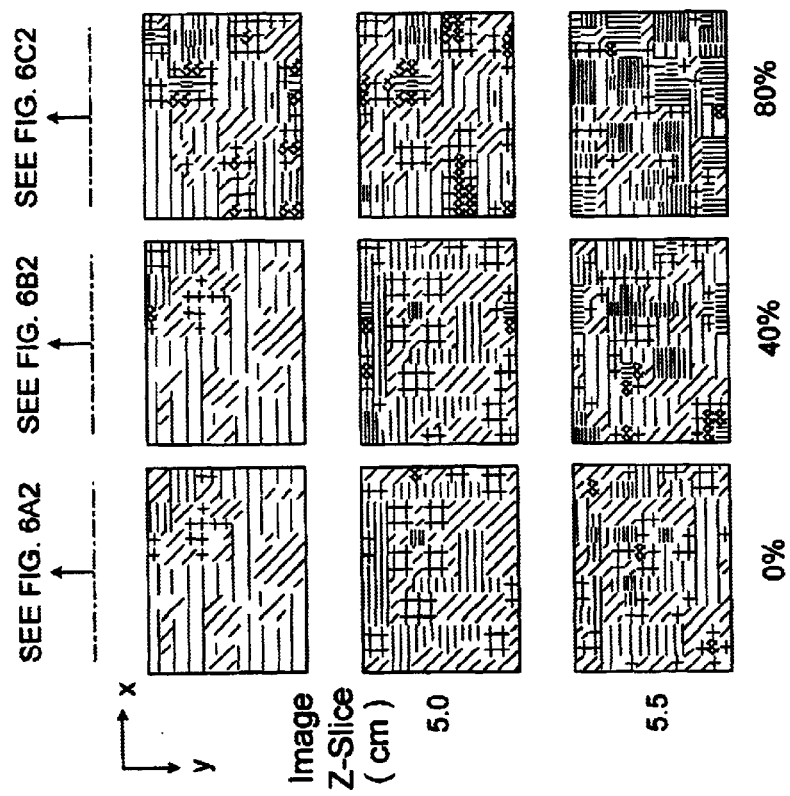

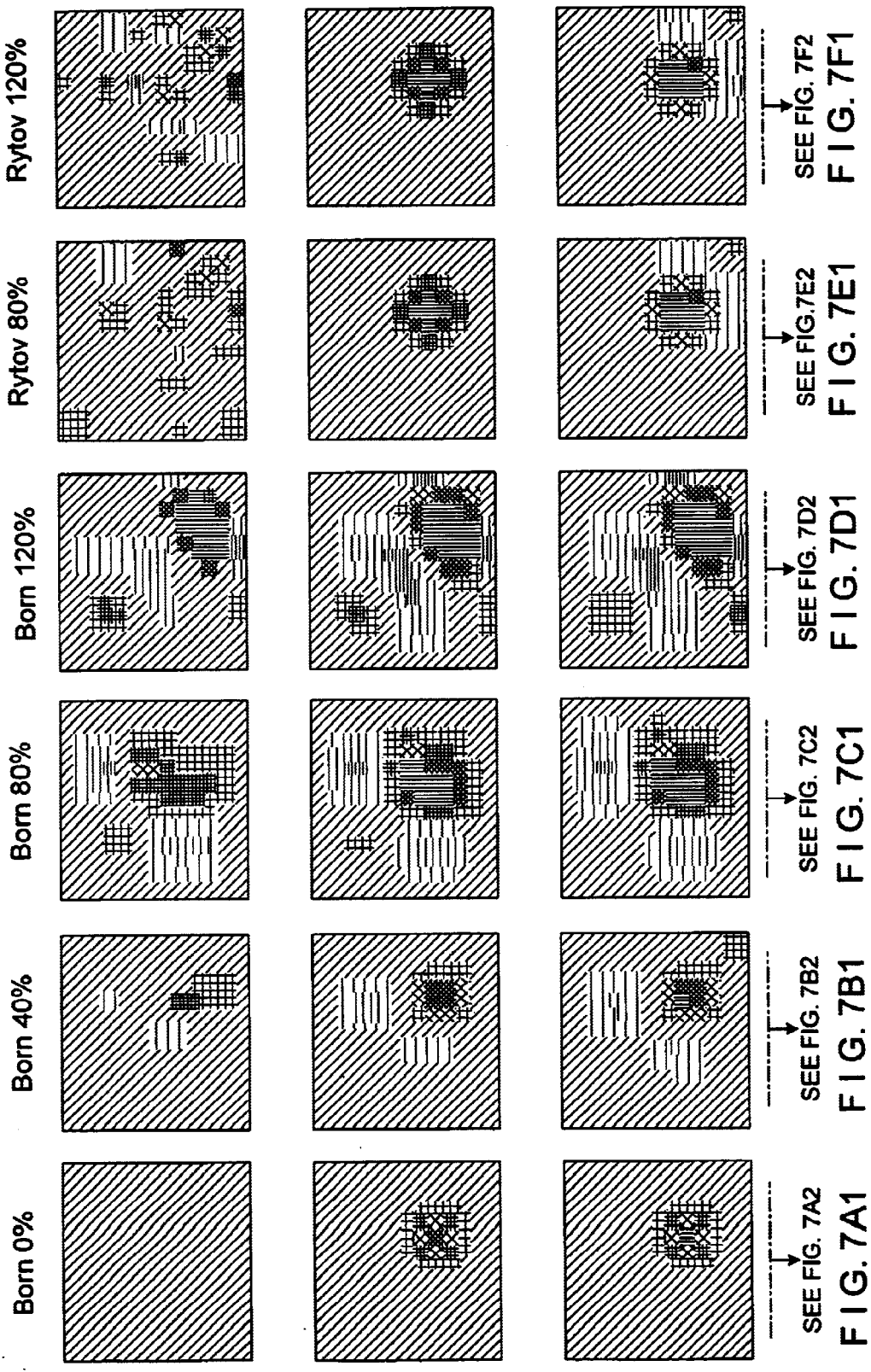

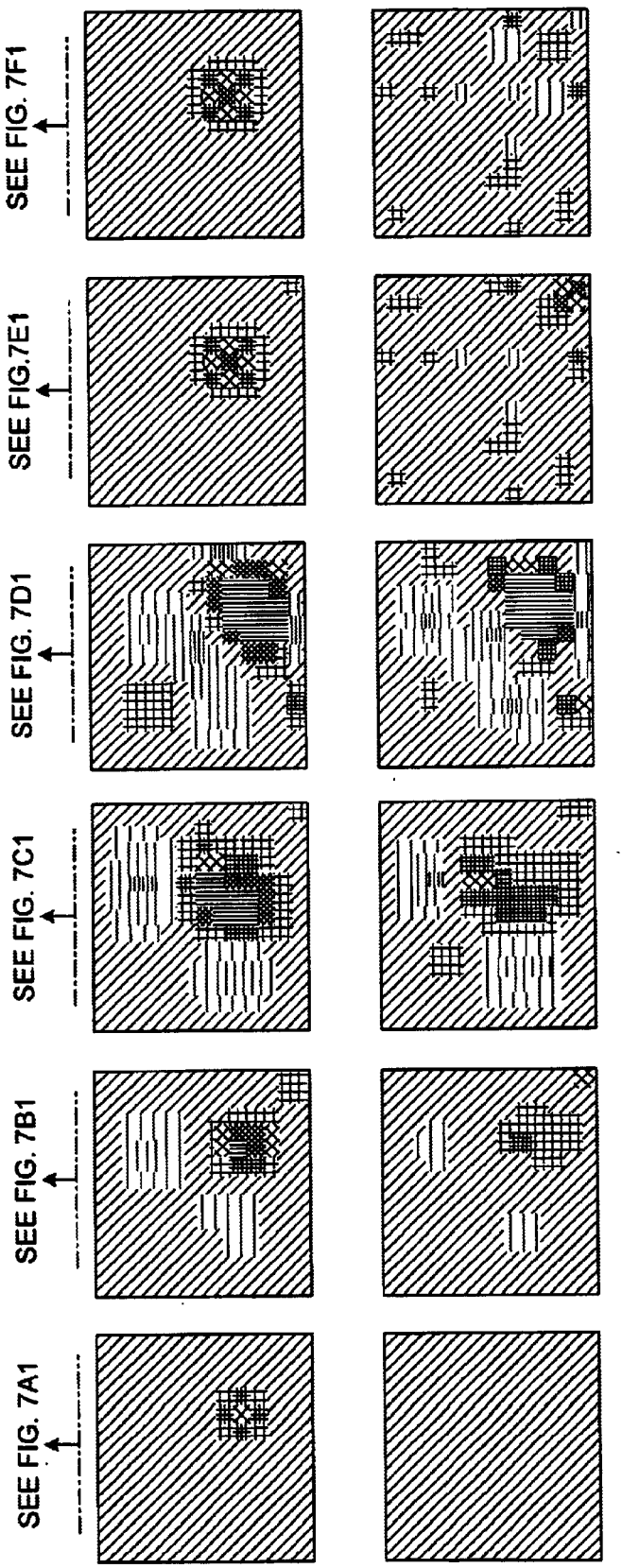

Image result without SD calibration

Image result with SD calibration

SYSTEM AND METHOD FOR ENABLING SIMULTANEOUS CALIBRATION AND IMAGING OF A MEDIUM

CROSS-REFERENCE TO A RELATED APPLICATION

This application claims priority from the Provisional Appln. No. 60/261,492 filed on Jan. 12, 2001, the entire disclosure of which is incorporated herein by reference.

STATEMENT AS TO FEDERALLY SPONSORED RESEARCH

This invention was made with Government support under grants from the National Institutes of Health, NIH R29-NS38842 and NIH P41-RR14075, and the U.S. Army, No. DAMD17-99-2-9001. As a result, the Government of the United States of America has certain rights to the invention.

TECHNICAL FIELD

The invention relates to imaging, and more particularly to calibration of optical methods of imaging highly scattering media.

BACKGROUND

Opaque media such as paint, milk, foam, emulsions, colloidal suspensions and human tissue do not strongly absorb visible light, while being optically turbid. This turbidity is a result of a very short scattering length characteristic of photons traveling within these media. The light does not travel in straight lines through such substances, and instead "diffuses" in a manner similar to heat flow. In other words, photons are multiply scattered within these media until they are either absorbed, or they exit the boundaries of the medium.

Recently, there has been a significant interest in the use of optical radiation for imaging within the highly scattering media, such as a biological tissue. Photons can travel within a highly scattering medium along a distribution of paths, of which very few are straight. Thus, the direction of the light into a highly scattering medium and a subsequent direction of the diffuse light emitted from the medium provides certain information regarding local variations in the scattering and absorption coefficients. Such information can identify, for example, a breast or brain tumor, bleeding in the brain, or aneurysm. Furthermore, multiple wavelengths can be used to spectroscopically determine local tissue concentrations of oxy-hemoglobin (HbO) and deoxy-hemoglobin (Hb) in tissue, which can vary in response to some stimulus, e.g., a drug. For a general description of such applications, see, e.g., A. Yodh et al., Physics Today, 34–40, March 1995.

If the spatially varying optical properties of a highly scattering medium are known, photon propagation within the medium can be calculated numerically. This numerical calculation is simplified when the scattering is much larger than the absorption, in which case photon propagation can be approximated as a diffusion process. This condition is typically satisfied in a biological tissue in the spectral range of about 700 to 900 nm. The numerical calculation gives the distribution of light inside a highly scattering medium, and is usually referred to as the "forward calculation." For a medium being imaged, however, the "inverse calculation" should be solved, e.g., by deducing the distribution of optical properties within the medium from the diffuse light measurements. Numerical techniques for performing the inverse calculation include singular value decomposition (SVD), simultaneous iterative reconstruction technique (SIRT), K-space diffraction tomography, and a use of an extended Kaman filter. For a general review of techniques for the forward and inverse calculations, see, e.g., S. R. Arridge, *Inverse Problems*, 15:841, 1999.

In the art of diffuse optical tomography ("DOT"), multiple sources sequentially direct the light into a highly scattering medium (e.g., tissue), at spatially separated locations. For each such source, multiple detectors on the tissue measure the diffuse light emitted from the sample at spatially separated locations. The detectors may further obtain one or more parameters of the diffuse light emitted, e.g., fluence, and then utilize those parameters as input in the inverse calculation. However, the measurements can include various errors caused by, for example, source and detector coupling to the tissue, source and detector positional uncertainties, fluctuations in the source power, and variations in the detector gain.

to minimize these uncertainties, DOT systems are typically calibrated with initial measurements for a known sample, and the calibration is used to correct the subsequent measurements for imaging an unknown sample. Unfortunately, errors can vary from a measurement to another measurement because of, e.g., the movement or perspiration of a patient or the movement of an optical fiber that forms part of a source or detector. Thus, the results of an inverse calculation can include experimental systematic errors caused by measurement variations that are independent of the medium's properties of interest. The experimental systematic errors can also limit absolute spectroscopic measurements of the optical properties at a particular spatial location, i.e., absolute, rather than relative, values of absorption and scattering.

International Application No. WO 01/19241 describes a calibration methodology for the diffuse optical measurements that corrects the transmittance measurements between a source and a detector for factors unrelated to sample properties. The calibration methodology is based on the same set of transmittance measurements that are subsequently corrected by the calibration, and then are used in imaging and/or spectroscopy applications. This calibration method involves a forward calculation for each of multiple source-detector pairs based on an approximate model of the sample, and a minimization of an expression that depends on the forward calculations and the transmittance measurements to determine self-consistent coupling coefficients for every source-detector pair. Once the coupling coefficients are determined, they are used to correct the transmittance measurements. An inverse calculation is performed on the corrected sample measurements to determine spatial variations in the optical properties of the sample.

SUMMARY OF THE INVENTION

The present invention is preferably based on the fact that by allowing source and detector calibration factors to vary freely in the inverse calculation and be determined simultaneously with image reconstruction, image artifacts can be significantly reduced.

In general, the present invention provides systems and methods for determining a distribution of one or more optical properties of a medium illuminated with radiation (e.g., electromagnetic radiation, infrared radiation, continuous-waive radiation etc.) from one or more sources, where the radiation exiting the medium is received by one or more detectors. The detectors may be adapted to obtain one or more parameters of the received radiation. Once the radiation is received and the parameters are obtained, one or more optical properties of the medium can be derived using at least one calibration factor and the received radiation, in which the calibration factors are variables. For a highly-scattering medium, the probability that photons entering the medium will scatter can significantly exceed the probability that photons entering the medium will be absorbed. Hence, employing diffusion approximation may be appropriate because the probability of scattering is at least an order of magnitude higher than the probability of absorption. Each source can be spatially separated from a respective detector, e.g. by two centimeters, and the separation selected can be limited by the experimental parameters (e.g., the number of sources and detectors, the radiation used, the size of the medium etc.). Where the medium is human tissue, the separation may be one or more centimeters.

The calibration factors used as variables in deriving one or more optical properties of the medium can include, for example, a source coupling factor, (which can be referred to interchangeably with a source strength or a detector gain), a detector coupling factor, a detector gain, a source location factor, and a detector location factor.

The optical properties may be derived as a continuous-wave data and include, e.g., the absorption and scattering. However, the optical properties may also be derived, for example, as a frequency-domain or time-domain data. In case that the derived optical properties are in the frequency domain, each would have a respective amplitude and phase. Alternatively, if the derived optical properties are in the time domain, each would have a respective amplitude and temporal off-set.

The or more of these optical properties can be derived by solving an inverse problem. The inverse problem can be solved by using, for example, a linear approximation model. One such exemplary linear approximation model used to derive the optical properties of the medium is a Born Approximation. Another exemplary linear approximation model is a Rytov Approximation. In the Rytov Approximation model, the measured parameter (e.g., fluence), is defined as an exponential of a perturbation on the background fluence. A specific implementation of an embodiment of the method of the present invention using the Rytov approximation involves minimizing a least-squares expression for the difference between the logarithms of the theoretical and measured fluence for each source-detector pair. The model can also scale the obtained parameters taken as input (e.g. fluence), to make those parameters dimensionless and to be on the same order as the calibration factors.

Some examples of the property distributions obtained from performing the calculations on these measured parameters may include an absorption distribution, a scattering distribution, a distribution of both, etc. The determined property distribution can be displayed in one or more images.

In another embodiment of the present invention, a computer-readable medium containing a program is provided that can cause a processor to receive radiation scattered through an illuminated medium as input. Also, the processor may be programmed so as to obtain one or more parameters of the received radiation as input. The program can further cause the processor to derive one or more optical properties of the medium by using the input and one or more calibration factors. The program can subsequently cause the processor to determine a property distribution using the derived optical properties. The property distribution may be provided as output. The program can use a non-linear or linear model to derive the optical properties of the media. Using the Rytov approximation model, the least-squares expression for the difference between the logarithms of the theoretical and measured fluence for each source-detector pair can be minimized so as to derive the optical properties, and determine the property distribution. The program can also scale all obtained parameters taken as input to make them dimensionless and to be of the same order as the freely varying source and detector calibration factors.

In yet another embodiment of the present invention, systems are provided for determining the distribution of one or more optical properties of a medium illuminated with radiation from one or more sources. These systems have one or more radiation detectors for receiving radiation. These systems also include a processor for deriving one or more optical properties from the received radiation and one or more calibration factors. The processor also determines the distribution using one or more properties of the medium.

The sources can have optical fibers and lasers, and the detectors may include optical fibers linked to photodetectors. To irradiate the medium, the system can use electromagnetic radiation, e.g., infrared radiation, or any continuous-wave radiation. The sources providing the radiation can be spatially separated from the detectors that receive the radiation. The spatially separated sources can extend in a plane opposite to a plane containing the detectors, and the spatial separation can be, e.g., two centimeters, and can be varied according to the experimental parameters (i.e., the number of sources and detectors, the radiation used, and the size of the medium). When the medium is human tissue, the separation can be one or more centimeters. The processor can also provide absorption coefficients, scattering coefficients, or both.

In addition, the property distribution determined by the system of the present invention can be provided as an image on a display, e.g., a computer screen. The model used to determine the property distribution can again be non-linear or linear. One such model includes the Rytov approximation and can involve, e.g., minimizing the square of the difference between the logarithms of the theoretical and measured fluence for each source-detector pair. The model can also utilize scaling parameters obtained from the signal as input to make them dimensionless and to be of the same order as the calibration factors.

in still another embodiment of the present invention, systems are provided for determining a distribution of one or more optical properties of a medium illuminated with radiation from one or more sources. These systems have means for receiving radiation exiting the medium, and means for deriving one or more optical properties of the medium using one or more calibration factors and the received radiation, in which the calibration factors are variables. Means for determining a distribution in the medium using the derived optical properties are also provided.

In yet another embodiment of the present invention, software systems are provided which, when executed on a processing device, may determine a distribution of one or more optical properties in a medium illuminated with radiation from one or more sources. These systems have a processing subsystem which, when executed on the processing device, configures the processing device to obtain parameters of received radiation exiting the medium, derive one or more optical properties of the medium using one or more calibration factors and obtained parameters, in which the calibration factors are variables, and determine a distribution in the medium using one or more derived optical properties.

Unless otherwise defined, all technical and scientific terms used herein have the same, or substantially similar, meaning as commonly understood by one of ordinary skill in the art to which the present invention belongs. Although methods and materials similar or equivalent to those described herein can be used in the practice or testing of the present invention, exemplary methods and materials are described below. In addition, the materials, methods, and examples are illustrative only and are in no way limiting. All cited references are incorporated herein by reference.

In prior art systems and methods, several potential experimental systematic errors can hamper the ability to obtain images of the distribution of properties within a medium by applying radiation. While the characteristics of a system can be modeled prior to experimentation, slight fluctuations during experimentation, including for example changes in source strength or detector gain, can cause significant image artifacts. By including calibration in the image reconstruction algorithm, the present invention provides a substantial image improvement, despite the presence of possible considerable experimental systematic errors. One advantage of the methods and systems of the present invention is their ability to obtain diffuse optical tomography images having considerably reduced artifacts. The new imaging methods of the present invention can also be applied in electrical impedance tomography. These imaging methods can be utilized to image spatially varying optical properties of biological media, e.g., tissue, with enhanced contrast. In addition, such novel methods can be applied to image non-biological media (e.g., plastics, ceramics, or liquids) to detect defects or impurities using radiation. Other features and advantages of the invention will be apparent from the following detailed description, and from the claims. According to the present invention, the source and detector calibration factors can be allowed to vary freely in the inverse calculation and be determined simultaneously with image reconstruction, and thus image artifacts can be significantly reduced.

BRIEF DESCRIPTION OF THE DRAWINGS

FIGS. 6A, 6B and 6C are exemplary images of simulated data obtained from the experimental geometry in FIG. 5 generated for 0%, 40% and 80% uncertainties, respectively, using a normalized Rytov approximation and excluding the reconstruction of freely varying source and detector coupling factors.

FIGS. 6D, 6E and 6F are exemplary images of simulated data obtained from the experimental geometry in FIG. 5 generated for 0%, 40% and 80% uncertainties, respectively, using a normalized Rytov approximation and including the reconstruction of freely varying source and detector coupling factors.

FIGS. 7A, 7B, 7C and 7D are images of simulated data obtained from the experimental geometry in FIG. 5 generated for 0%, 40%, 80% and 120% uncertainties, respectively, using a Born approximation and including the reconstruction of freely varying source and detector coupling factors.

FIGS. 7E and 7F are images of simulated data obtained from the experimental geometry in FIG. 5 generated for 80% and 120% uncertainties, respectively, using a normalized Rytov approximation and including the reconstruction of freely varying source and detector coupling factors.

DETAILED DESCRIPTION

Figure 1:
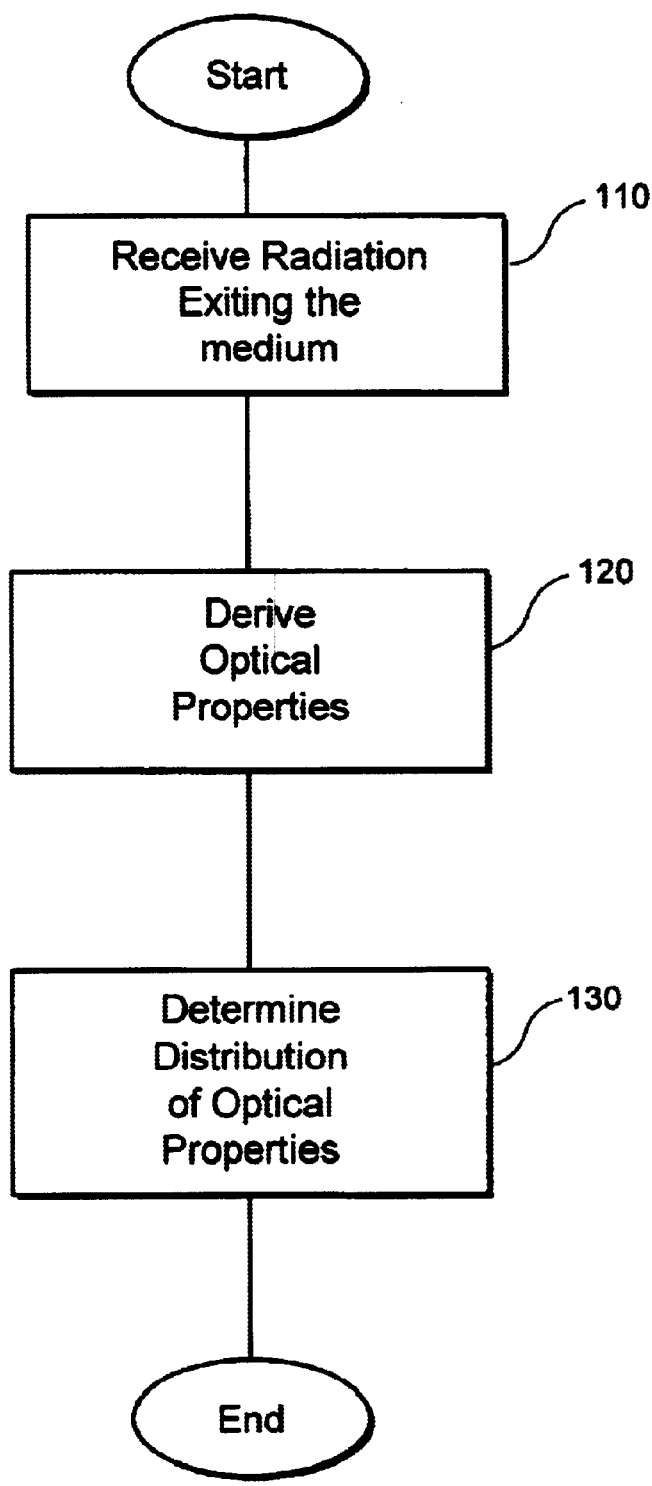
FIG. 1 is a top-level block diagram illustrating an exemplary embodiment of a method according to the present invention.

The novel methods of the present invention calibrate sources and detectors as part of the inverse calculation for image reconstruction to reduce image artifacts.

General Methodology

Research in diffuse optical tomography has rapidly progressed in moving the imaging modality from the development stage of computer simulations and phantom experiments to the application stage of imaging animal and human subjects. However, little work has discussed the importance and solution of experimental details that degrade image quality including, without limitation, the treatment of boundary conditions for solving the forward problem, source and detector coupling to tissue, source and detector positional uncertainties, and intrinsic tissue heterogeneity. The novel calibration techniques according to the present invention are based on the principle that, e.g., the inclusion of calibration factors as variables in the image reconstruction algorithm significantly improves the image quality.

The calibration techniques of the present invention can be applied to determine a property distribution within a scattering medium, which is an ill-posed, non-linear inverse problem. A linear approximation can be obtained by assuming the variations may be described as small perturbations in absorption and scattering, $\delta\mu_\alpha$ and $\delta\mu_s'$, respectively, around known background values of absorption and scattering, $\mu_{\alpha o}$ and $\mu_{so}'$, respectively. As indicated previously, one or more parameters of diffuse light emitted through a scattering medium may be obtained and used as input in the inverse calculation. One of those parameters is preferably fluence. A linear approximation of the measured fluence $\Phi$ can be obtained as a perturbation $\Phi_{pert}$ on a background fluence $\Phi_o$. In imaging, the fluence $\Phi$ is measured experimentally and the perturbation $\Phi_{pert}$ (which is caused by spatial variation in the radiative properties of the sample) should preferably be calculated.

An accurate determination of the perturbation $\Phi_{pert}$ prefers a calibration of a source and a detector, and a reasonable estimate of the background fluence $\Phi_o$. Errors in the determination of the calibration factors are likely to result in a highly localized absorption and scattering perturbations appearing adjacent to the sources and detectors as a compensation for the errors in the image reconstruction process. This type of image noise can be evidenced by high frequency spikes appearing preferentially near source and detector locations.

The exemplary methods of the present invention allow for the calibration by enabling the calibration factors to vary freely in the inverse calculation, and determining them as part of the image reconstruction algorithm. There are various calibration factors, e.g., source and detector coupling factors s and d, respectively, and source and detector location factors $r_s$ and $r_d$, respectively. By considering the logarithm of the measured fluence $\Phi$ as input into the image reconstruction algorithm, the perturbation $\Phi_{pert}$ becomes linearly dependent on the logarithms of s and d. However, the perturbation $\Phi_{pert}$ can remain non-linearly dependent on the optical properties of the sample. To obtain a linear dependence on the optical properties, an approximation, e.g., the Rytov or Born approximation, can be used, and the problem thus can become completely linear.

The Forward Problem:

The radiative transport equation provides a rigorous theory to describe radiation emitted from a medium. It may be applied to the migration of photons through highly scattering media, such as biological tissue. This approach can indicate that near-infrared photons in highly scattering media e.g., human and animal tissue, essentially undergo a random walk, since the scattering probability greatly exceeds the absorption probability. The propagation of these photons through a highly scattering medium can therefore be described by a diffusion approximation to the radiative transport equation. This exemplary diffusion can be provided as an equation as follows:

$$-\nabla \cdot (D(r)\nabla\Phi(r,t)) + v\mu_\alpha(r)\Phi(r,t) + \frac{\partial\Phi(r,t)}{\partial t} = vS(r,t), \quad (1)$$

where D(r) is the photon diffusion coefficient, $\Phi(r,t)$ is the photon fluence at position r and time t, v is the speed of light in the medium, $\mu_\alpha(r)$ is the absorption coefficient, and S(r,t) is the source; distribution of photons (see, e.g., A. Ishimaru, *Wave Propagation and Scattering in Random Media*, Academic Press, Inc. San Diego, 1978; M. S. Patterson et al., *Applied Optics* 28:2331, 1989; R. C. Haskell et al., *Journal of the Optical Society of America A*, 11:2727, 1994). The photon diffusion coefficient D(r) is defined by the equation:

$$D(r) = \frac{v}{3\mu_s'(r) + \alpha\mu_\alpha(r)}, \quad (2)$$

where $\mu_s'(r)$ is the reduced scattering coefficient. The coefficient $\alpha$ can be variously set to three, zero, or some other value (see, e.g., D. J. Durian, *Optics Letters*, 23:1502, 1998, R. Aronson and N. Corngold, *Journal of the Optical Society of America A*, 16:1066, 1999).

When focusing on the variations in the absorption, the value selected for $\alpha$ is moot, and therefore it can preferably be set to zero.

When the distribution of properties within the medium varies spatially, two approaches can be used to find approximate solutions to Equation (1): the Born approximation (see, e.g., A. Ishimaru, *Wave Propagation and Scattering in Random Media*, Academic Press, Inc. San Diego, 1978; A. C. Kak and M. Slaney, *Principles of Computerized Tomographic Imaging*, IEEE Press, New York, 1988), and the Rytov approximation (see, e.g., A. C. Kak and M. Slaney, *Principles of Computerized Tomographic Imaging*, IEEE Press, New York, 1988). The Born approximation can preferably be defined as:

$$\Phi = \Phi_o + \Phi_{pert}. \quad (3)$$

The Rytov approximation is preferably:

$$\Phi = \Phi_o \exp(\Phi_{pert}). \quad (4)$$

Each approach decomposes the total fluence $\Phi$ into the background fluence $\Phi_o$, which only depends on the background optical properties $\mu_{\alpha o}$ and $\mu_{so}'$, and $\Phi_{pert}$, which is linearly related to the spatial variations in the optical properties $\delta\mu_\alpha$ and $\delta\mu_s$. For the Rytov approximation, assuming absorption variations only, the perturbation can be calculated as follows:

$$\Phi_{pert}(r_s, r_d) = -\frac{1}{\Phi_o(r_s, r_d)} \int \Phi_o(r_s, r) \frac{v\delta\mu_\alpha}{D_o} G(r, r_d) dr, \quad (5)$$

where $r_s$ and $r_d$ are the respective positions of the source and detector, $D_o$ is the diffusion coefficient for the chosen $\alpha$, and G is the Green's function of the photon diffusion equation for the background optical properties provided by the boundary conditions. If the background is homogeneous, G can be expressed analytically for some simple geometries (see, e.g., M. S. Patterson et al., Applied Optics 28:2331, 1989; R. C. Haskell et al., *Journal of the Optical Society of America A*, 11:2727, 1994; S. R. Arridge et al., *Physics in Medicine and Biology*, 37:1531, 1992).

One exemplary geometry to which Equation (4) can be applied is a slab, i.e., a geometry where the sources are in a single plane on one side of the sample and the detectors are in a plane on the opposite side thereof. In this geometry, the extrapolated zero-boundary condition can be applied to the above-described radiative transport problem to solve for the Green's function G of the diffusion equation for the background optical properties (see, e.g., R. C. Haskell et al., *Journal of the Optical Society of America A*, 11:2727, 1994). The background fluence $\Phi_o$ is related to the Green's function by the source and detector coupling factors. The source coupling factor s includes source power and a coupling to the medium. The detector coupling factor d includes detector gain and a coupling to the medium. Using s and d respectively, to represent the source and detector coupling factors, the background fluence is as follows:

$$\Phi_o(r_s, r_d) = sdG(r_s, r_d) \quad (6)$$

The Inverse Problem:

By solving the inverse problem, the images of spatially varying optical properties can be generated from measurements of the fluence $\Phi$. The inverse problem includes solving a least-squares equation. For the Rytov approximation, the expression to minimize can be as follows:

$$F(x) = \sum_{i=1}^{N_{meas}} [\ln \Phi_{Theory,i}(x) - \ln \Phi_{Meas,i}]^2, \quad (7)$$

where the index i is summed over the measurements for each source-detector pair, $\Phi_i(x)$ is provided by Equations (4) and (5) where x is a vector giving $\delta\mu_\alpha$ at each voxel position, and $\Phi_{Meas}(x)$ is the measured fluence for each source-detector pair.

For the case of fewer measurements than unknowns, the linear problem is underdetermined, and can be described by the (regularized) Moore-Penrose generalized inverse:

$$\hat{x} = -A^T (AA^T + \lambda I)^{-1} y, \quad (8)$$

where I is the identity matrix, and $\lambda$ is the Tikhonov regularization parameter. Each element of the matrix A can be defined as:

$$A_{i,j} = -\frac{v}{D_o \Phi_o(r_{s,i}, r_{d,i})} \Phi_o(r_{s,i}, r_j) G(r_j, r_{d,i}), \quad (9)$$

where $r_{s,i}$ and $r_{d,i}$ are the positions of the $i^{th}$ source and the $i^{th}$ detector, respectively. The position of the $j^{th}$ voxel is expressed as $r_j$. Using the Rytov approximation, each element of y can be as follows:

$$y_i = \ln\left[\frac{\Phi(r_{s,i}, r_{d,i})}{\Phi_o(r_{s,i}, r_{d,i})}\right]. \quad (10)$$

In one exemplary approach, $\lambda$ can be set to $10^{-3}$ of the maximum eigen-value of $AA^T$ (see, e.g., H. Dehghani et al., *Physiological Measurement*, 20:87, 1999; V. Kolehmainen et al., *Physiological Measurement*, 18:289, 1997).

Image and Calibration Factor Reconstruction

Calibration for the Source and Detector Coupling Factors and Image Reconstruction Image quality depends on accurate knowledge of the background optical properties, $\mu_{\alpha o}$ and $\mu_{so}'$, and the source and detector calibration factors s and d. Therefore, estimates of the matrices A and y similarly depend on these quantities.

By considering $\mu_{\alpha o}$ and $\mu_{so}'$ as known properties, the inverse problem can be solved for the calibration factors.

As described above, the measurements can include various errors caused by, for example, source and detector coupling to the medium, fluctuations in source power, variations in detector gain, and source and detector positional uncertainties. Hence, the measurements can be calibrated for the source and detector coupling and intensity fluctuations (source and detector coupling factors), as well as for their positions (source and detector location factors).

In the case when measurements should be calibrated for the source and detector coupling factors s and d (the source and detector coupling and fluctuations in the source power and the detector gain), an augmented model of a particular measurement, $y_i$ may be written in terms of the unknown source coupling factors $s_k$, the detector coupling factors $d_l$, and the absorption perturbations $\delta\mu_{\alpha j}$. The source and detector coupling factors can preferably refer to both coupling fluctuations and intensity fluctuations of the sources and detectors. Using these variables, the particular measured parameter (in this case fluence) may be expressed as follows:

$$y_i = \ln\left[\frac{\Phi(r_{s,i}, r_{d,i})}{\Phi_o(r_{s,i}, r_{d,i})}\right] = \ln[s_{k(i)}] + \ln[d_{l(i)}] + \sum_j A_{i,j} \delta\mu_{\alpha,j}, \quad (11)$$

where k(i) and l(i) identify the source and detector, respectively, which are used for the $i^{th}$ measurement.

In case that numerous measurements are conducted, the measured parameter (fluence) can be written in a matrix form as:

$$y = B\xi, \text{ where } B = [\tilde{A}SD], \quad (12)$$

where S is a source coupling factor matrix, D is a detector coupling factor matrix, and $\tilde{A}$ is a matrix A rescaled by a factor of $\mu_{\alpha o}$.

Factor $\xi$ is defined by the formula:

$$\xi = \left[\frac{\delta\mu_{\alpha,1}}{\mu_{\alpha o}} \ldots \frac{\delta\mu_{\alpha,N_v}}{\mu_{\alpha o}} \ln s_1 \ldots \ln s_{N_s} \ldots \ln d_1 \ldots \ln d_{N_d}\right], \quad (13)$$

where $N_v$ is the number of voxels, $N_s$ is the number of sources, and $N_d$ is the number of detectors. $\delta\mu_{\alpha j}$ can be scaled by $\mu_{\alpha o}$ to make the elements dimensionless and being of the same order as ln s and ln d. Scaling these quantities to make them dimensionless and of the same order as the logarithms of the calibration parameters yields a normalized formulation.

As indicated previously, $\tilde{A}$ is a rescaling of the matrix A whose terms are defined by Equation (9) by a factor of $\mu_{\alpha o}$. Thus, $$\tilde{A} = \mu_{\alpha o} A. \quad (14)$$

Matrices S and D have block diagonal form. For example, S has a one in the $k^{th}$ column for each measurement corresponding to source k, and D has a one in the $l^{th}$ column for each measurement corresponding to detector l. Thus, with four measurements between two sources and two detectors, the following matrix is defined:

$$[S \; D] = \begin{bmatrix} 1 & 0 & 1 & 0 \\ 1 & 0 & 0 & 1 \\ 0 & 1 & 1 & 0 \\ 0 & 1 & 0 & 1 \end{bmatrix}$$

Calibration for the Source and Detector Location Factors and Image Reconstruction Conversely, if the measurements should be calibrated for the source and detector locations, an augmented model of a particular measurement, $y_i$, may be defined in terms of the uncertain source location $\delta r_{sk}$, uncertain detector location $\delta r_{dk}$ and the absorption perturbations $\delta \mu_{aj}$. In this exemplary augmented model, $y_i$ may be expressed as:

$$y_i = \ln\left[\frac{\Phi(r_{s,k(i)}, r_{d,l(i)})}{\Phi_o(r_{s,k(i)}, r_{d,l(i)})}\right] \quad (15)$$

$$= \left[\frac{1}{\Phi_o(r_{s,k(i)}, r_{d,l(i)})}\right]\nabla_{s,k(i)}\Phi(r_{s,k(i)}, r_{d,l(i)}) \cdot \delta r_{s,k(i)} +$$

$$\frac{1}{\Phi_o(r_{s,k(i)}, r_{d,l(i)})}\nabla_{d,l(i)}\Phi(r_{s,k(i)}, r_{d,l(i)}) \cdot \delta r_{d,l(i)} +$$

$$\sum_j A_{i,j}\delta\mu_{\alpha,j},$$

where $k(i)$ and $l(i)$ identify the source and detector, respectively, used for the $i^{th}$ measurement. It should be noted that $\delta r_{sk}$ and $\delta r_{dl}$ represent the differences from the respective assumed values as used in $\Phi_0$ and the real values for the measurement of $\Phi$. In addition, $\delta r_{sk}$ and $\delta r_{dl}$ can be vector quantities representing the uncertainties in the x, y, and z coordinates of the corresponding source or detector.

For this exemplary embodiment of the present invention, in case that numerous measurements are conducted, the measured parameter (fluence) can be written in a matrix form as follows:

$$y = B\xi, \text{ where } B = [\tilde{A}P_sP_d] \quad (16)$$

where $\xi$ is defined by:

$$\xi = \left[\frac{\delta\mu_{\alpha,1}}{\mu_{\alpha 0}} \ldots \frac{\delta\mu_{\alpha,N_v}}{\mu_{\alpha 0}} \frac{\delta r_{s,1}}{\sigma} \ldots \frac{\delta r_{s,N_s}}{\sigma} \frac{\delta r_{d,1}}{\sigma} \ldots \frac{\delta r_{d,N_d}}{\sigma}\right] \quad (17)$$

in which $N_v$ is the number of voxels, $N_s$ is the number of sources, and $N_d$ is the number of detectors. Scaling $\delta\mu_{\alpha j}$ by $\mu_{\alpha o}$ and the positional unknowns by $\sigma$ makes the elements dimensionless. $\sigma$ can be selected so as to make the unknowns of the same order of magnitude, and in this manner, $\sigma$ is preferably an estimate of the expected error in the source and detector locations. Similarly, $\tilde{A}$ is a rescaling of the matrix A whose terms are given by Equation (9) by a factor of $\mu_{\alpha o}$. Thus, $$\tilde{A} = \mu_{\alpha o} A. \quad (18)$$

Matrices $P_s$ and $P_d$ can have a block diagonal form. For example, $P_s$ may be non-zero in the $k^{th}$ column for each measurement corresponding to source k, and $P_d$ may be non-zero in the $l^{th}$ column for each measurement corresponding to detector l. These preferably have the same form as the [S D] matrix provided above with respect to the image reconstruction including the calibration for the source and detector coupling factors.

Frequency Domain Formulation

The imaging method according to the present invention is not limited to using continuous-wave radiation. In the frequency domain, the measured parameters of amplitude and phase may also be obtained. If the measured parameters are in the frequency domain, then, for example, the source and detector coupling factors have corresponding unknown phases $\theta_s$ and $\theta_d$, respectively. They also likely have unknown amplitudes $A_s$ and $A_d$. The ln s and ln d, which appear in Equation (13), can be complex, as are the corresponding elements in the matrix A. To separate the real and imaginary portions of the complex matrix, the real portions can be stacked on top of the imaginary portions, i.e., $$B = \begin{bmatrix} \text{re}(\tilde{A}) & \text{re}(S) & \text{re}(D) \\ \text{im}(\tilde{A}) & \text{im}(S) & \text{im}(D) \end{bmatrix} \quad (19)$$

In the frequency domain, should be adjusted as follows:

$$\xi = \left[\frac{\delta\mu_{\alpha,1}}{\mu_{\alpha 0}} \ldots \frac{\delta\mu_{\alpha,N_v}}{\mu_{\alpha 0}} \ln A_{s_l} \ldots \ln \right. \quad (20)$$

$$\left. A_{N_s}\theta_{s_l} \ldots \theta_{N_s}\ln A_{d_l} \ldots \ln A_{d_{N_s}}\theta_{d_l} \ldots \theta_{N_d}\right].$$

For the case of four measurements between two sources and two detectors, the complex matrix can be:

$$[S \; D] = \begin{bmatrix} 1 & 0 & i & 0 & 1 & 0 & i & 0 \\ 1 & 0 & i & 0 & 1 & 0 & i & 0 \\ 0 & 1 & 0 & i & 0 & 1 & 0 & i \\ 0 & 1 & 0 & i & 0 & 1 & 0 & i \end{bmatrix} \quad (21)$$

The example of a formulation for the case where there are uncertain source and detector locations si substantially similar to the example provided above. In particular, Equation (19) would be provided as follows:

$$B = \begin{bmatrix} \text{re}(\tilde{A}) & \text{re}(P_S) & \text{re}(P_D) \\ \text{im}(\tilde{A}) & \text{im}(P_S) & \text{im}(P_D) \end{bmatrix}. \quad (22)$$

Time Domain Formulation

The imaging method according to the present invention can also be applied to measurements taken in the time domain. To obtain time domain data, each source provides a temporally coherent pulse of radiation, e.g., a picosecond light pulse, and the detectors are time-gated to measure the temporal delay of the radiation in addition to its intensity. For a general reference on such time-domain techniques in diffuse optical tomography see, e.g., M. S. Patterson et al., *Applied Optics* 28:2331, 1989; S. R. Arridge, *Inverse Problems*, 15:841, 1999. Therefore, to apply the new calibration methods to time-domain data, the calibration factors s and d are described by corresponding unknown amplitudes and temporal off-sets. The unknown amplitudes in the time-domain are treated in the same fashion as in the continuous-wave domain. The unknown temporal off-sets represent a non-linear perturbation and can be reconstructed using a non-linear form of the model.

The example of a formulation for the case where there are uncertain source and detector locations si substantially similar to the example provided above.

Exemplary Illustrations of the System and Method of the Present Invention

Referring to FIG. 1, a top-level block diagram presenting an exemplary embodiment of a method according to the present invention is illustrated. Initially, the radiation which exits from the medium is received (step 110). Then, in step 120, one or more optical properties of the medium are derived using the radiation received in step 110 and one or more calibration factors, wherein the calibration factors are variables. Subsequently, in step 130, a distribution of the optical properties in the medium is determined using the optical properties derived in step 120. The details of steps 110–130 are described in detail herein above.

Figure 2:
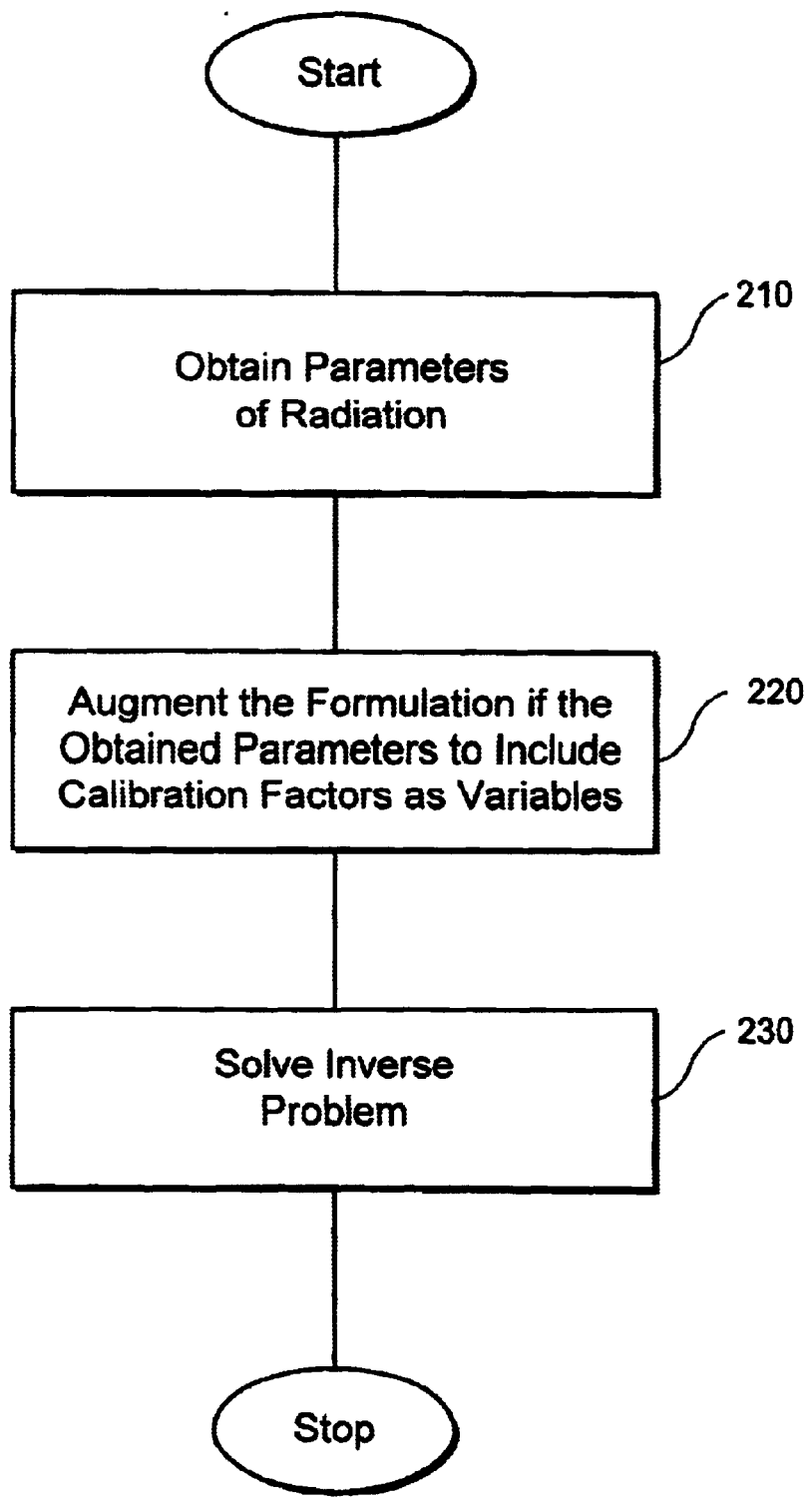
FIG. 2 is a more detailed block diagram illustrating a step of deriving optical properties of the method shown in FIG. 1.

Further details for step 120 of deriving one or more optical properties of the medium are additionally illustrated in FIG. 2 and described below. In particular, parameters of radiation are obtained in step 210. One of such parameters can be fluence. The detectors with which the radiation exiting the medium is received may be adapted to directly measure the parameters of the radiation, e.g., fluence. Alternatively, the parameters may be calculated using the data corresponding to the received radiation, Once the parameters are obtained in step 210, the formulation of each obtained parameter can be augmented to include the calibration factors as variables (step 220). As described above, the calibration factors may include the source coupling factor, detector coupling factor, source location factor and detector location factor. Subsequent to augmenting the formulations of the obtained parameters of radiation, one or more optical properties of the medium are derived as output by solving an inverse problem in which the augmented formulations are used as input (step 230).

General System

Figure 3:
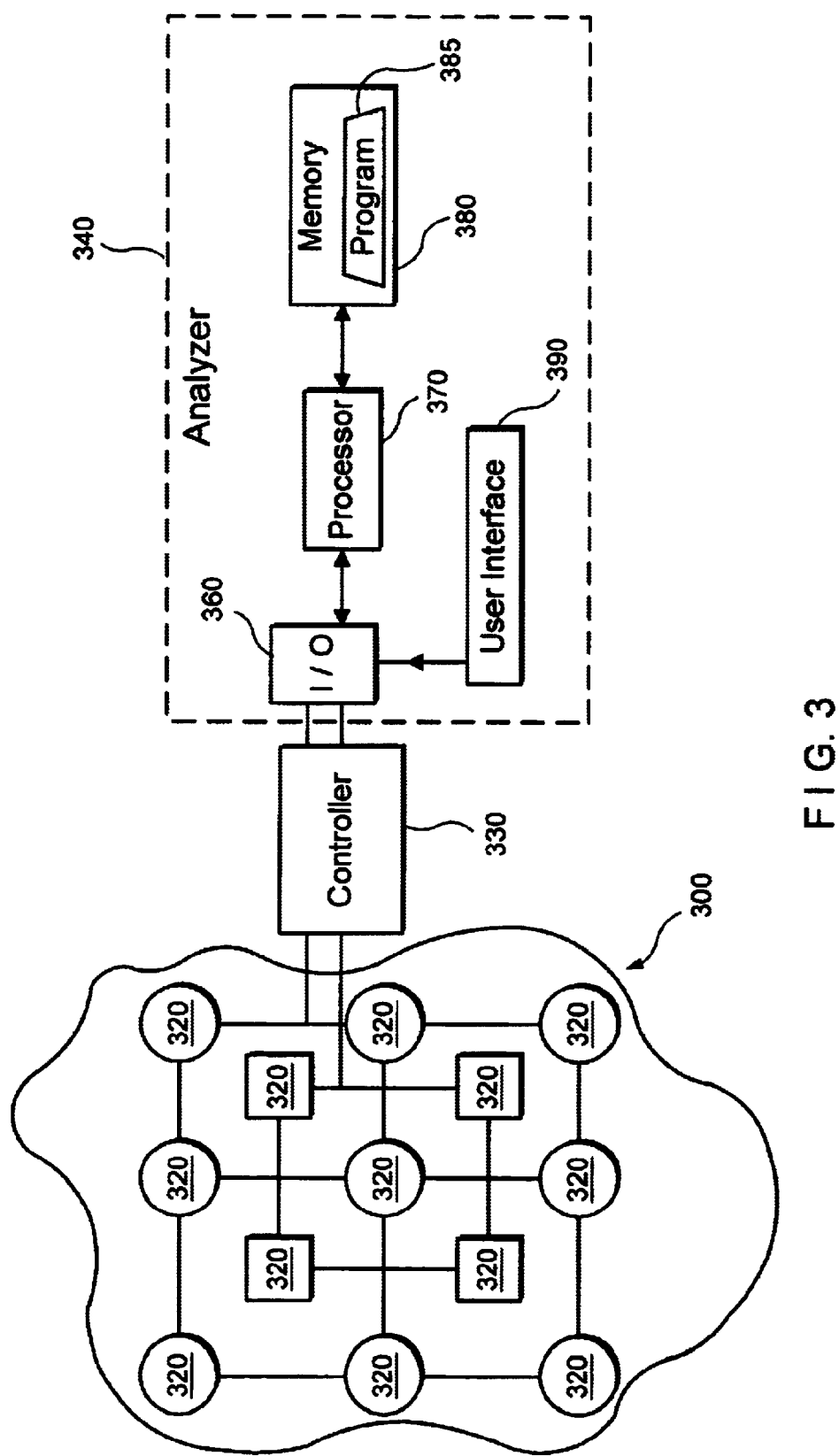
FIG. 3 is a schematic diagram of an exemplary embodiment of a diffuse optical tomography system according to the present invention.

FIG. 3 shows an exemplary embodiment of the system capable of executing the method according to the present invention in which experimental systematic errors may cause significant image artifacts. Such system can be a diffuse optical tomography ("DOT") system 300. The system 300 includes an array of spatially separated light sources 310 and spatially separated detectors 320. During use, the array of sources 310 and detectors 320 can be positioned over a sample 350 to be imaged, e.g., a patient's head or breast. A controller 330 connected to the light sources 310 can sequentially trigger them to forward or provide light into the sample 350, so that a highly scattering medium may cause the light to become diffuse within the sample. For each sequentially triggered source, each detector 320 receives light that reaches it through sample 350 to obtain the measured fluence $\Phi$. The controller 330 is also connected to the detectors 320, and selectively channels the signals from the detectors 320. An analyzer 340 is connected to the controller 330 and analyzes the signals generated by detectors 320.

Figure 4:
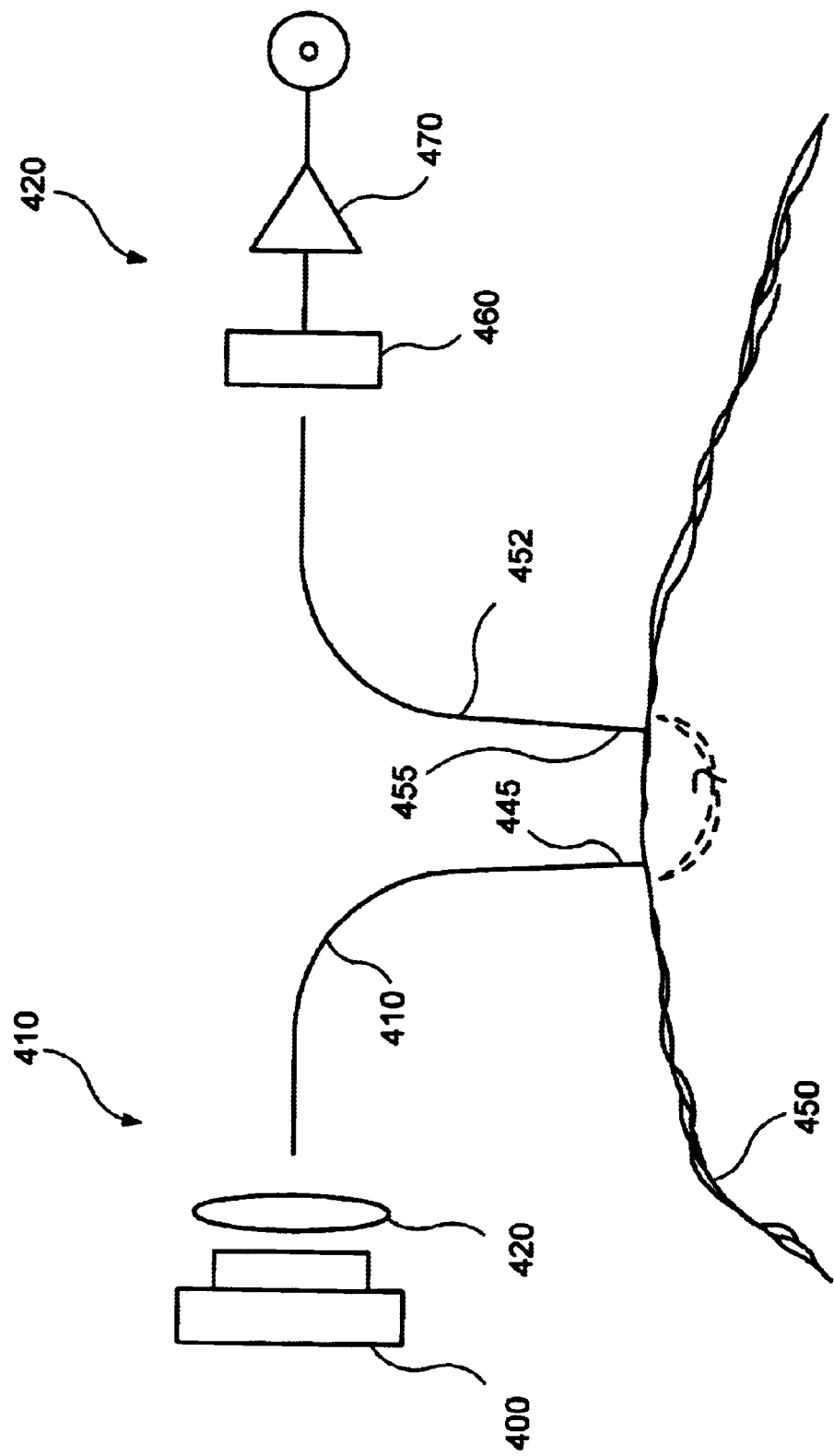
FIG. 4 is a schematic diagram of an exemplary source-detector pair for the system of FIG. 1.

For example, in one exemplary embodiment shown in FIG. 4, each source 310 may include a diode laser 400 for producing optical radiation and a lens 420 for coupling the optical radiation into an optical fiber 410. The optical fiber 410 has an end 415 adjacent to the sample 450 for directing the optical radiation into the sample 450. Each detector 420 includes an optical fiber 452 having an end 455 adjacent to the sample 450 for receiving the optical radiation exiting the sample 450, a photodetector 460 for measuring the intensity of the optical radiation received by the optical fiber 452, and an amplifier 470 for amplifying the output of the photodetector 460.

To obtain information about the optical properties of the sample 450 from the fluence, it is preferable to consider the measured fluence $\Phi$ as representing the perturbation $\Phi_{pert}$ on a background fluence $\Phi_o$. According to Equation (4), this can be accomplished by using the Rytov approximation. By minimizing the least-squares expression as provided in Equation (7), the analyzer 340 can simultaneously obtain the optical properties of the sample and conduct source and detector calibration.

In other embodiments of the present invention, the light source can include a laser other than a diode laser, e.g., an ultrafast laser, or may be an incoherent source. Also, the sources can include a common light source that selectively couples light into multiple fibers that deliver the light to spatially separated locations on the sample. Alternatively, the sources need not include optical fibers at all. For example, the lasers themselves can be positioned adjacent to the sample or can include beam delivery optics to direct the light to the sample through free space. Furthermore, the light sources can provide light at multiple wavelengths by including, for example, multiple diode lasers.

In the description provided below, it can be assumed that the sources provide continuous-wave optical radiation, and that the detectors measure the intensity of the optical radiation.

It should be understood that the calibration techniques described herein can also be applied to other measurement techniques in which the sources do not provide continuous-wave radiation. For example, in some techniques, the amplitude of optical radiation provided by the sources can be modulated to create photon density waves in the sample, and the detectors are configured to measure the amplitude and phase of the photon density waves after propagation through the sample. For a general reference on "DOT" techniques with modulated optical radiation, see, e.g., M. A. O'Leary et al., *Phys. Rev. Lett.* 69, 2658 (1992). Furthermore, in other techniques, each source can provide a temporally coherent light pulse, for example, a picosecond pulse, and the detectors may be time-gated to measure the temporal delay of the diffuse light pulse in addition to its intensity. For a general reference on such time-domain DOT techniques, see, e.g., M. S. Patterson et al., *Appl. Opt.* 28:2331, 1989, and S. R. Arridge, *Inverse Problems*, 15:841, 1999.

Exemplary Applications

The methods and systems of the present invention provide the ability to obtain images of spatially varying optical properties within highly scattering media, such as human and animal tissue, and can therefore be used to address many new biomedical problems and applications. For example, these novel methods and systems can be used to image a region of tissue to ascertain the presence of an early tumor, a small amount of bleeding, or an early aneurysm. In another exemplary application, multiple wavelengths can be used to evaluate local tissue concentrations of chemicals, such as hemoglobin, within tissue. Also, the methods and systems of the present invention can be further combined with use of a chemical stimulus to determine the chemical response.

Non-biomedical applications for the methods and systems of the present invention also exist and can be used to image materials such as plastics, ceramics, and liquids for defects or impurities. In addition, the methods and systems of the present invention can be used for identifying regions of interest having distinct optical properties within highly scattering media, such as concealed objects, without invasive study of that media. For example, the methods of the present invention can be used to image an optical heterogeneity within a diffusive liquid. Furthermore, the novel calibration methods and systems can also be applied in electrical impedance tomography.

Software Implementation

The calibration methods can be implemented in hardware, software, or a combination of both. The methods can be implemented via computer programs using standard programming techniques following the methods, equations, and Figures described herein. Program code can be executed using a processing arrangement which can receive input data to perform the functions described herein and generate output information. The output information can be applied to one or more output devices, such as a display monitor, printer etc.

Each program can preferably be implemented in a high-level procedural or object-oriented programming language to communicate with a general computer system. However, the programs can be implemented in assembly or machine language, if desired. In any case, the computer language can be a compiled or interpreted language.

Each computer program can preferably be stored on a storage medium or device (e.g., ROM, magnetic diskette, or optical disc) readable by a general or special purpose programmable processing arrangement, for configuring and operating the computer when the storage media or device is read by the processing arrangement to perform the procedures and techniques described herein. The computer program can also reside in cache or main memory during program execution. The processing methods can also be implemented as a computer-readable storage medium, configured with a computer program, where the storage medium so configured can cause the processing arrangement to operate in a specific and predefined manner so as to perform the functions and techniques described herein.

For example, referring again to FIG. 3, the analyzer 340 includes a processor 370, an input/output control card 360, a user interface 390 such as a keyboard and monitor, and memory 380. The memory 380 stores a program 385 specifying the steps of the calibration method. When executed, the program 385 causes the processor 370 to carry out the steps of the method according to the present invention.

EXAMPLES

The methods and systems of the present invention are further described in the following examples, which do not limit the scope of the invention described in the claims and are provided merely for illustrative purposes.

Example 1
Simulation of Image Reconstruction

Figure 5:
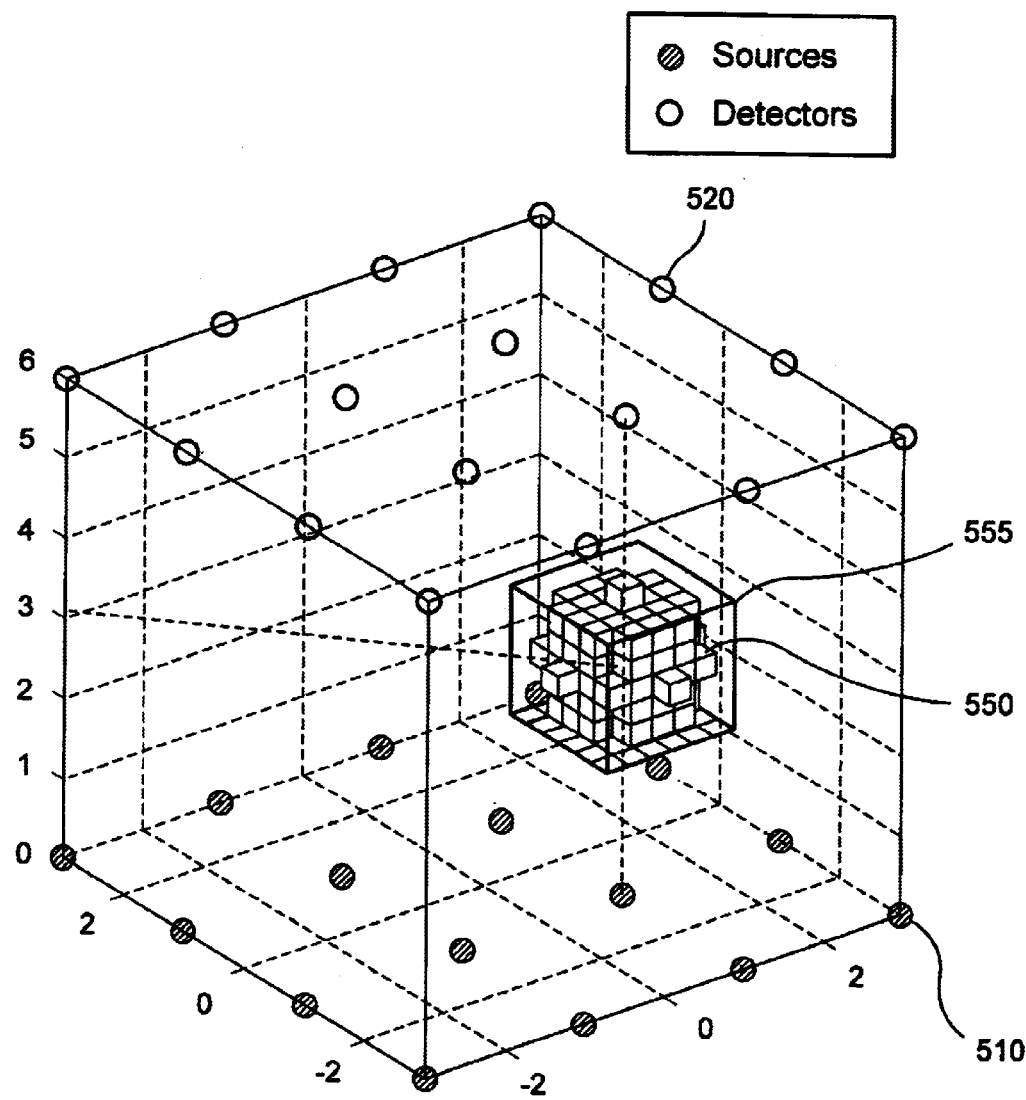
FIG. 5 is a diagram of a first example of an experimental geometry derived using the present invention.

Several advantages of the methods of the present invention were demonstrated by simulations. The results obtained utilizing a normalized Rytov approximation without the reconstruction of calibration factors (i.e., without using the new calibration methods), a normalized Rytov approximation with reconstruction, a Born approximation with reconstruction, and a Rytov approximation without normalization were compared. A diagram of a first example of an experimental geometry is shown in FIG. 5.

The computer simulation involved the transmission through a 6-cm thick slab with background optical properties $\mu_{so}'=10$ cm$^{-1}$ and $\mu_{ao}=0.15$ cm$^{-1}$. A 1.6-cm diameter absorbing object 550 with $\mu_{so}'=10$ cm$^{-1}$ and $\mu_{ao}=0.15$ cm$^{-1}$ was centered at (x, y, z)=(1, −1, 3) cm. Sixteen sources 510 were programmed in a four-by-four grid at z=0, spaced 2 cm apart to span x=−3 to 3 cm and y=−3 to 3 cm. Similarly, sixteen detectors 520 were located in a four-by-four grid at z=6, spanning x=−3 to 3 cm and y=−3 to 3 cm in 2-cm steps. All simulated measurements were made with continuous-wave sources.

The Full Born expansion was used to solve the forward problem. A 1.6×1.6×1.6 cm cube 555 divided into 7×7×7 voxels was centered over the 1.6-cm diameter absorbing object 550.

Initially, the source and detector coupling factors were varied, namely, the source and detector amplitudes. The source and detector amplitudes were chosen randomly from a normal distribution with a mean of 1. The effect of different standard deviations (0%, 40%, and 80%) was investigated. The normal distribution was biased by discarding negative amplitudes. A separate instance of the source and detector amplitude variation was considered for each standard deviation. There was no additive measurement noise (i.e., shot noise or electronic noise) in the simulated data, just the model error associated with the source and detector amplitudes.

For the inverse problem, voxel centers were distributed from x=−3 to 3 and y=−3 to 3 in 0.5-cm steps and z=0.5 to 5.5 in 0.5-cm steps. There were 1859 voxels, each with dimensions of 0.5×0.5×0.5 cm. The source and detector amplitudes were assumed to be all equal to 1. Two different inverse problems were considered: (1) Rytov without coupling, and (2) Rytov with coupling. In each case, Tikhonov regularization was used to obtain the pseudo-inverse, since the system matrix is under-determined and ill-conditioned.

FIGS. 6A–6F show the results obtained with the normalized Rytov approximation both excluding the reconstruction of the source and detectors coupling factors (FIGS. 6A–6C), and including such factors (FIGS. 6D–6F). FIGS. 6A and 6D show results for 0% uncertainty in source and detector strengths, FIGS. 6B and 6E depict images for 40% uncertainty, and FIGS. 6C and 6F reflect 80% uncertainty. All images span X and Y from −3 to 3 cm, and Z-slices are vertically arranged from 0.5 (top) to 5.5 cm (bottom).

The results in FIGS. 6A–6C show images without the reconstruction of the source and detectors coupling factors, i.e., the effect of neglecting experimental systematic errors in the calibration. With no variance (i.e., no systematic error in the sources and detectors), the object is localized to the correct voxel in X and Y and is within 1 voxel (0.5 cm) in Z. The amplitude of the object is slightly underestimated due to blurring. While it is expected that $\delta\mu_a=0.10$ cm$^{-1}$, the reconstruction yields $\delta\mu_a=0.098$ cm$^{-1}$. The image contains artifacts near the sources and detectors. These artifacts disappear when the Born approximation is used for the forward problem, indicating that it arises from mismatch between the exact forward solution and the Rytov approximation for the inverse model (i.e., it results from model noise unrelated to source and detector calibration factors).

As the standard deviation in the calibration factors increases from FIG. 6A to FIG. 6C, it is still possible to ascertain the object, but this deviation has reduced the contrast relative to the surrounding voxels, and its amplitude is smaller than that in the voxels closest to the sources and detectors. The artifact amplitudes may greatly exceed the displayed contrast, and have been truncated to preserve contrast sensitivity sufficient to reveal the object of interest. The model noise caused by an incorrect calibration of the source and detector calibration factors (i.e. systematic errors in s and d) clearly degrades the image quality by increasing the artifacts.

FIGS. 6D–6F show the reconstruction results where the source and detector coupling factors are simultaneously determined with the optical properties of the sample using the novel calibration methods of the present invention. Without the variance in the calibration factors, the location of the object remains properly resolved in X and Y coordinates and is within 0.5 cm in Z coordinate. The resolution in FIGS. 6D–6F, with the simultaneous reconstruction of the calibration factors, is poorer than in FIGS. 6A–6C, due to its lacking this simultaneous reconstruction. The presence of more unknowns in the inverse calculation using simultaneous reconstruction explains the decrease in the resolution. By contrast, the artifact shown in FIG. 6A due to the error between the exact and the Rytov approximation to the forward problem is reduced using the simultaneous reconstruction. The reconstruction appears to compensate for the model mismatch in the Rytov approximation.

Comparing the images generated using the simultaneous reconstruction of the source and detector coupling factors (shown in FIGS. 6D–6F) to the corresponding images generated without reconstruction (shown in FIGS. 6A–6C) reveals a significantly improved image quality using the reconstruction. For both 40% and 80% variance, the image quality using the reconstruction in fact remains as good as the case where there is no variance. The minor differences are masked within the contrast sensitivity. While the reconstruction may not accurately determine the independent source and detector coupling factors with the sample, it assists with the accurate determination of the source-detector coefficient products (e.g., $s_k d_l$) for each measurement. Despite the uncertainties of 80%, the results shown in FIGS. 6D–6F indicate that the source-detector coefficient products can be determined within an accuracy of a few percent. In addition, it has been observed that, when additive shot or electronic measurement noise is included in the simulation, there may be a greater sensitivity to the measurement noise as the source and detector variance increases.

FIGS. 7A–7F show images of simulated data obtained from the experimental geometry in FIG. 5 generated for 0%, 40%, 80% and 120% uncertainties, respectively, using a Born approximation including the reconstruction of freely varying source and detector coupling factors. FIGS. 7E and 7F are images of simulated data obtained from the experimental geometry in FIG. 5 generated for 80% and 120% uncertainties, respectively, using a normalized Rytov approximation including the reconstruction of freely varying source and detector coupling factors. FIGS. 7A–7F are useful to compare use of the Born approximation with the reconstruction of the source and detector coupling factors to use of the normalized Rytov approximation with the reconstruction. FIGS. 7A–7D show results for 0% uncertainty to 120% uncertainty in the source and detector strengths. By comparison, FIGS. 7E and 7F depict images for 80% and 120% uncertainty using the Rytov approximation. The Z-slices are vertically arranged with each image spanning X and Y axes from −3 to 3 cm.

Images generated using the Born approximation are clearly inferior to those generated using the Rytov approximation for the same level of uncertainty. Indeed, the images generated using the Rytov approximation for uncertainties of 80% (FIG. 7E) and 120% (FIG. 7F) resemble those generated using the Born approximation at 0% (FIG. 7A) and 40% uncertainty (FIG. 7B) more than images using the Born approximation at a comparable level of uncertainty (FIGS. 7C and 7D). The standard Born implementation of the image reconstruction problem is non-linear with respect to the source and detector coupling factors. Therefore, if the initial estimate for the coupling factors is off by more than approximately 10%, simultaneously solving for the coupling factors may not lead to an improved result. By using the Rytov implementation (i.e., taking the logarithm of the data), the dependence on the source and detector factors is made linear, and it is then possible to accurately reconstruct the coupling factors despite an initial guess, possibly off by several hundred percent.

Figures 8A, 8B, 8C, 8D:
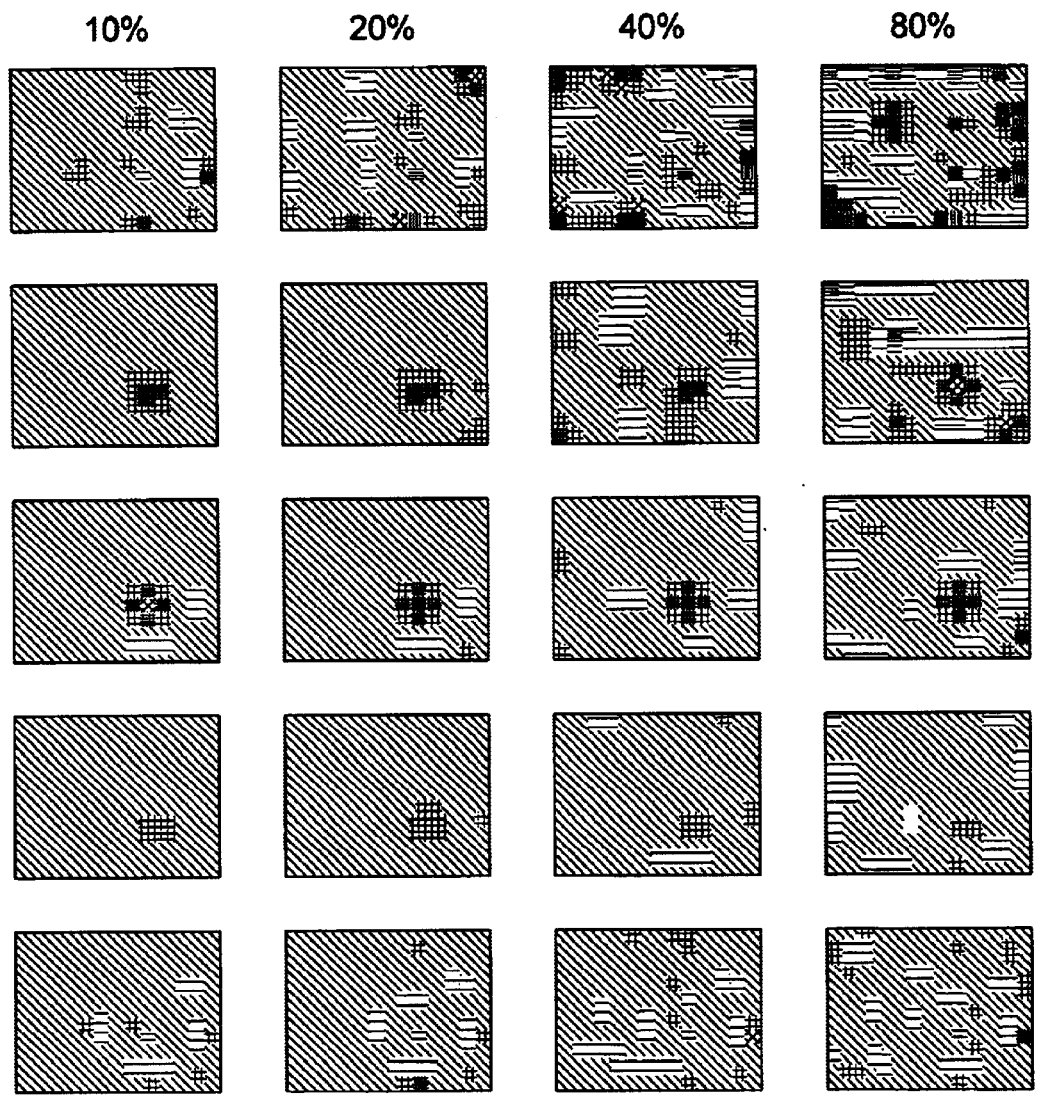
FIGS. 8A, 8B, 8C, and 8D are images, similar to those of FIGS. 7A–7F, of simulated data obtained from the experimental geometry in FIG. 5 generated for 10%, 20%, 40% and 60% uncertainties, respectively, using a Rytov approximation with the reconstruction of freely varying source and detector coupling factors, but without the normalization.

While merely substituting the Rytov approximation for the Born approximation offers an improved image quality, the normalization of the different factors in the inverse calculation (i.e., absorption, scattering, and calibration factors) can also contribute to the enhanced image quality. The normalization has a beneficial effect because the reconstruction of several different factors simultaneously is difficult if the factors differ in magnitude by an appreciable amount. Using the normalization, the reconstruction can proceed accurately over a larger range of values. FIGS. 8A–8D show the exemplary images using the Rytov approximation with the reconstruction of the source and detector coupling factors, but without the normalization. FIG. 8A shows the results for 10% uncertainty, FIG. 8B for 20%, FIG. 8C for 40%, and FIG. 8D for 60%: FIGS. 8A–8D have the same X-Y scale and arrangement of Z slices as in FIGS. 7A to 7F for an ease of comparison. Comparing FIGS. 8A–8D with FIGS. 7E and 7F reveals that normalizing results in the improved image quality, even at higher levels of uncertainty.

Alternatively, a different set of calibration factors may be varied. For example, the source and detector locations may be varied randomly with a normal distribution with a mean of 0. The effect of different distribution widths (0.1, 0.5, and 1.0 mm) was investigated. A separate instance of the source and detector amplitude variation was considered for each distribution width. There was no additive measurement noise (i.e. a source or detector electronic noise) in the simulated data, and only the model error associated with the source and detector locations was added.

For the inverse problem, voxel centers were distributed from x=−3 to 3 and y=−3 to 3 in 0.5 cm steps and z=0.5 to 5.5 in 0.5 cm steps. Approximately 1859 voxels were provided with dimensions of 0.5×0.5×0.5 cm. The vector $\xi$ in Equation (14) was initialized to zeros. Two different inverse problems were considered: (1) the Rytov approximation without the localization, and (2) the Rytov approximation with the localization. In each case, the Tikhonov regularization was used to obtain the pseudo-inverse since the system matrix was under-determined and ill-conditioned.

Figure 9A:
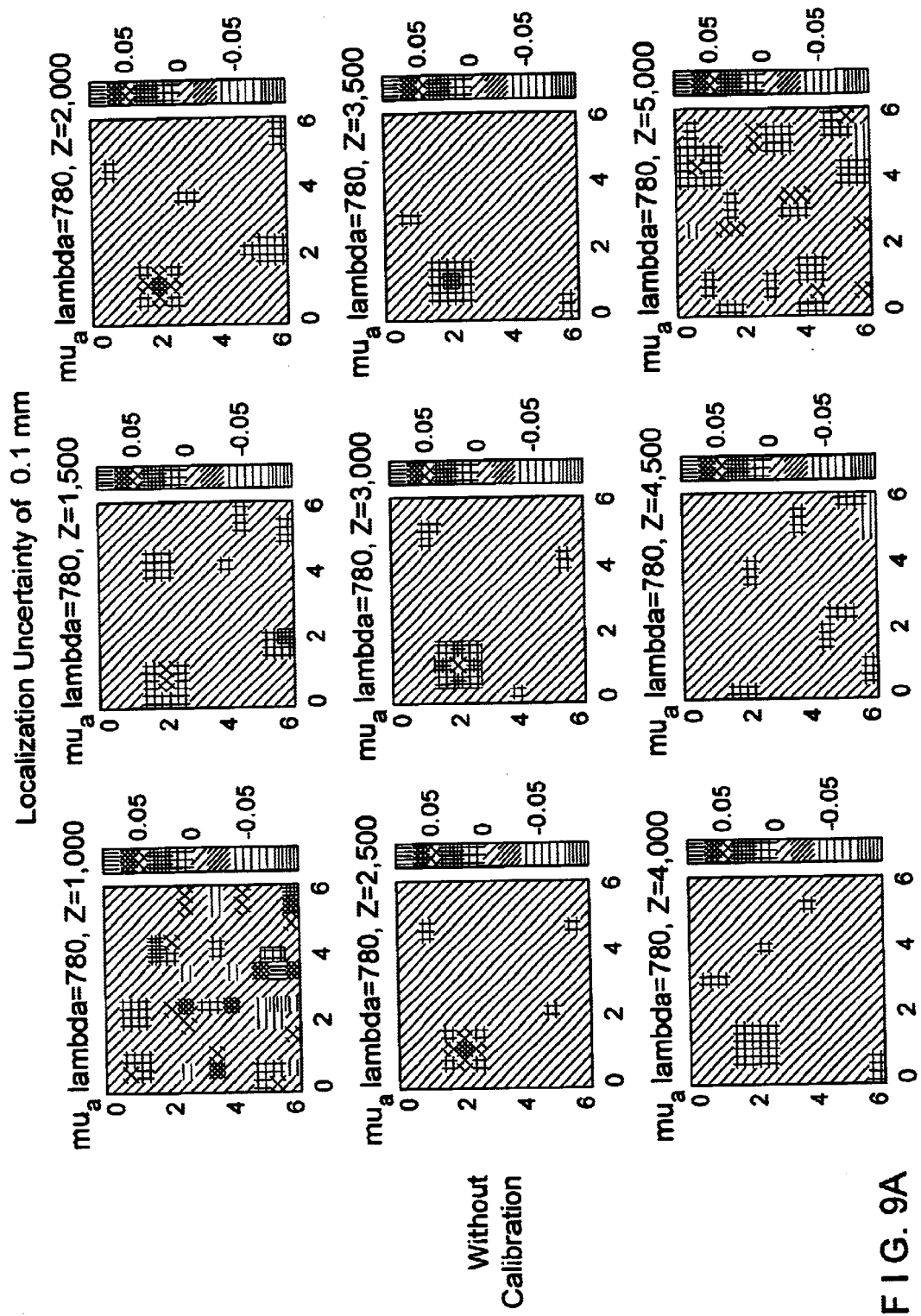
FIG. 9A is a set of images of simulated data obtained from the experimental geometry in FIG. 5, generated for localization uncertainty of e.g., 0.1 mm using a normalized Rytov approximation and excluding the reconstruction of freely varying source and detector location factors.
Figure 9B:
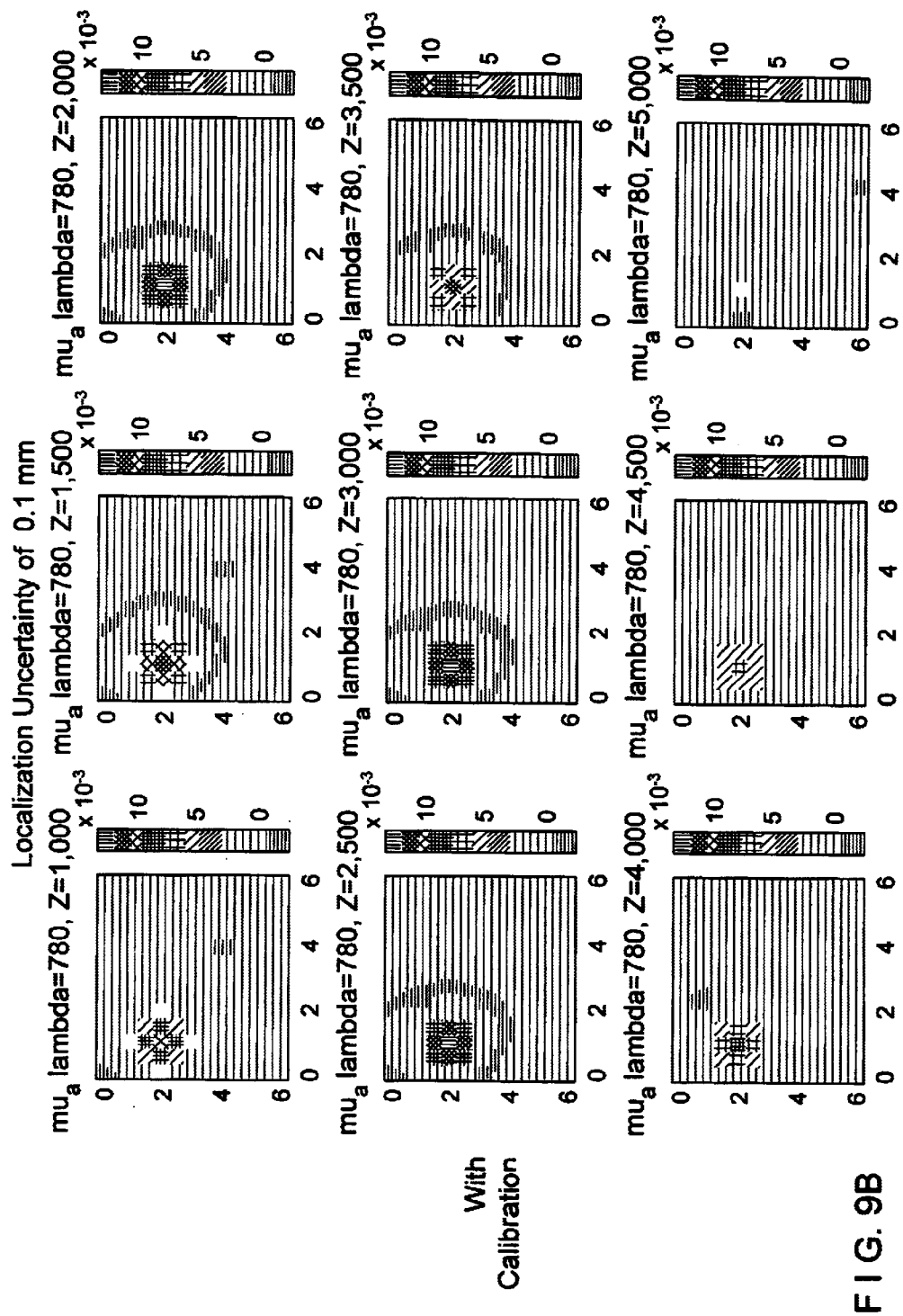
FIG. 9B is a set of images of simulated data obtained from the experimental geometry in FIG. 5, generated for localization uncertainty of e.g., 0.1 mm using a normalized Rytov approximation and including the reconstruction of freely varying source and detector location factors.
Figure 10A:
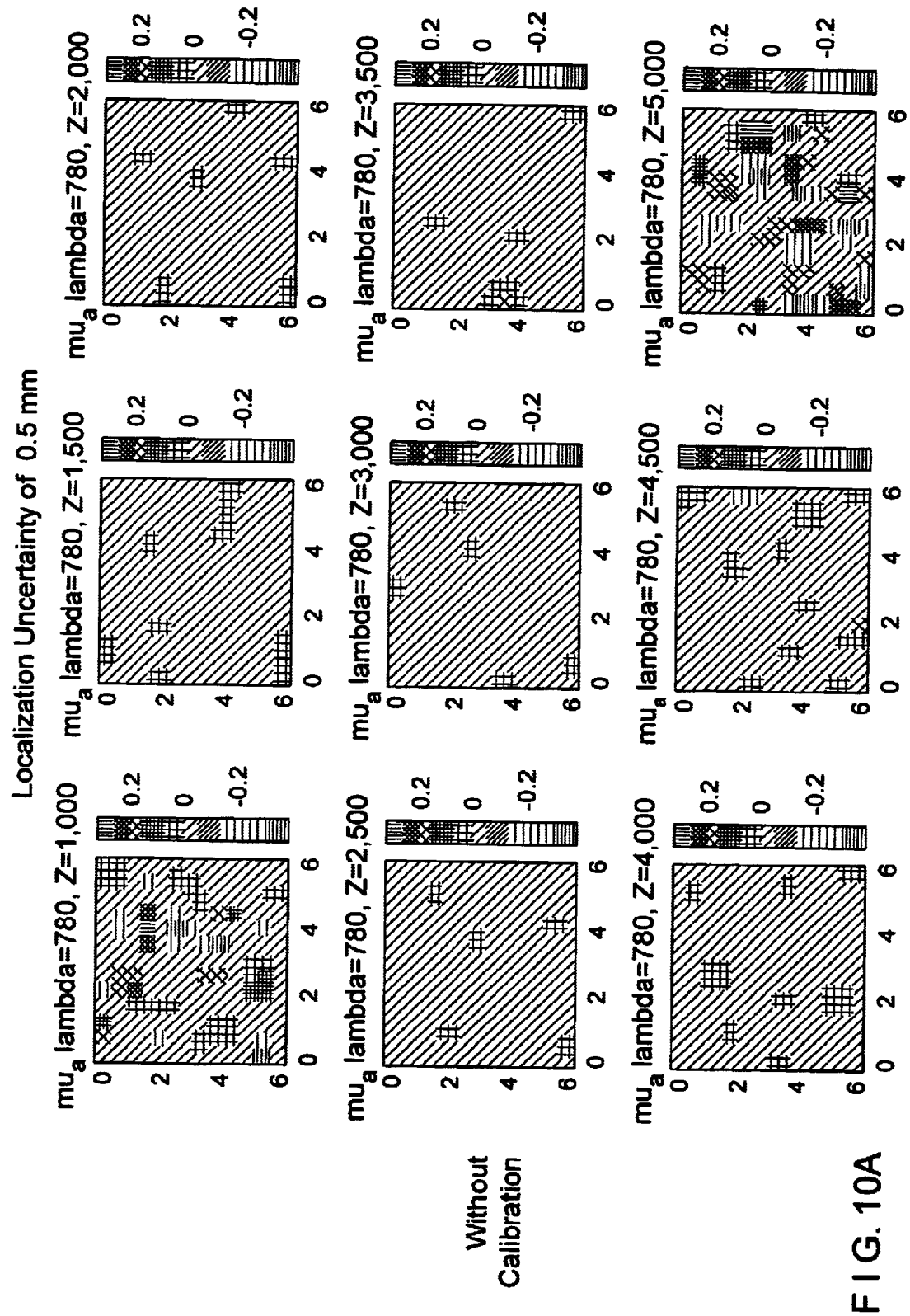
FIG. 10A is a set of images of simulated data obtained from the experimental geometry in FIG. 5, generated for localization uncertainty of e.g., 0.5 mm using a normalized Rytov approximation and excluding the reconstruction of freely varying source and detector location factors.
Figure 10B:
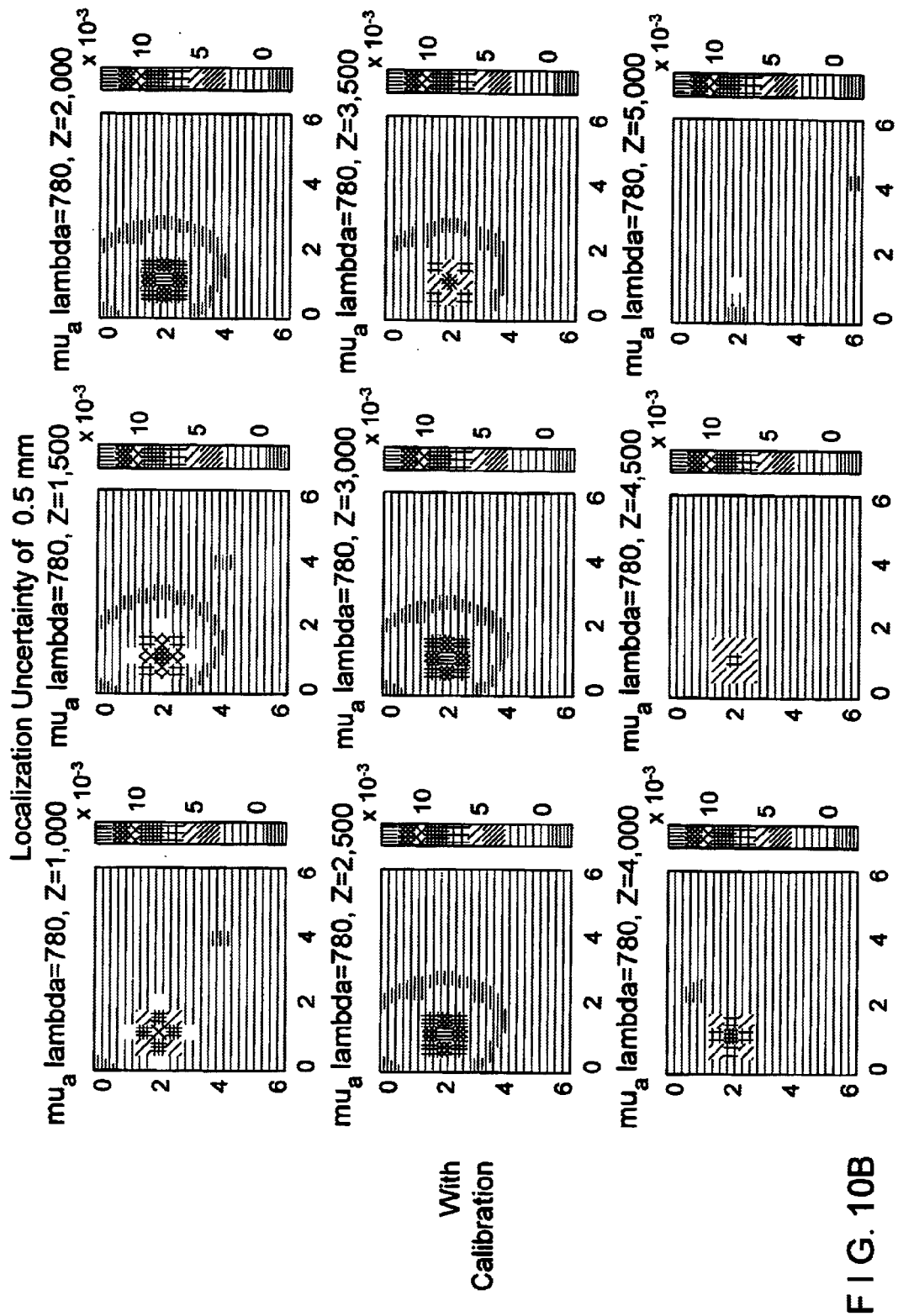
FIG. 10B is a set of images of simulated data obtained from the experimental geometry in FIG. 5, generated for localization uncertainty of e.g., 0.5 mm using a normalized Rytov approximation and including the reconstruction of freely varying source and detector location factors.
Figure 11A:
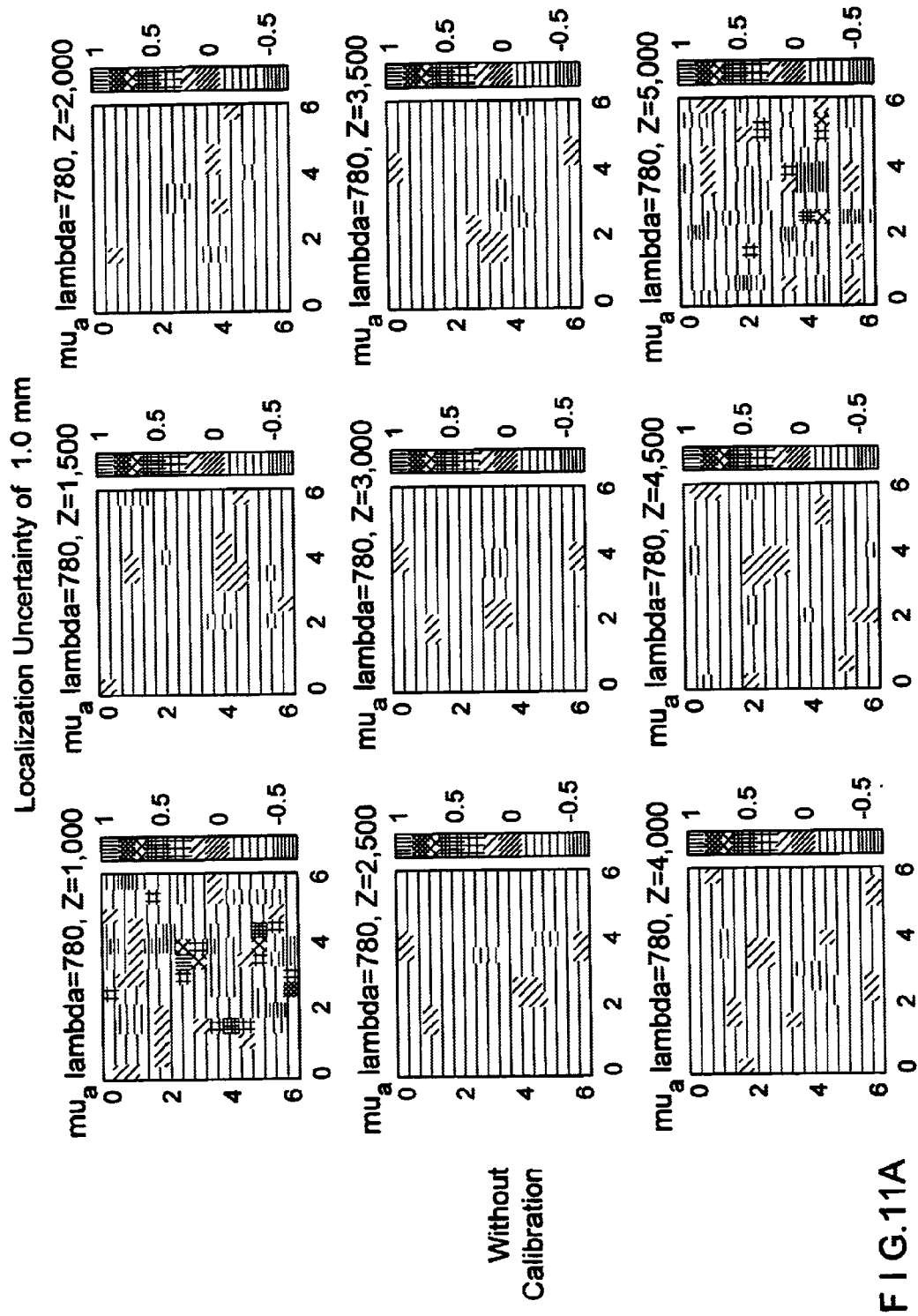
FIG. 11A is a set of images of simulated data obtained from the experimental geometry in FIG. 5, generated for localization uncertainty of e.g., 1.0 mm using a normalized Rytov approximation and excluding the reconstruction of freely varying source and detector location factors.
Figure 11B:
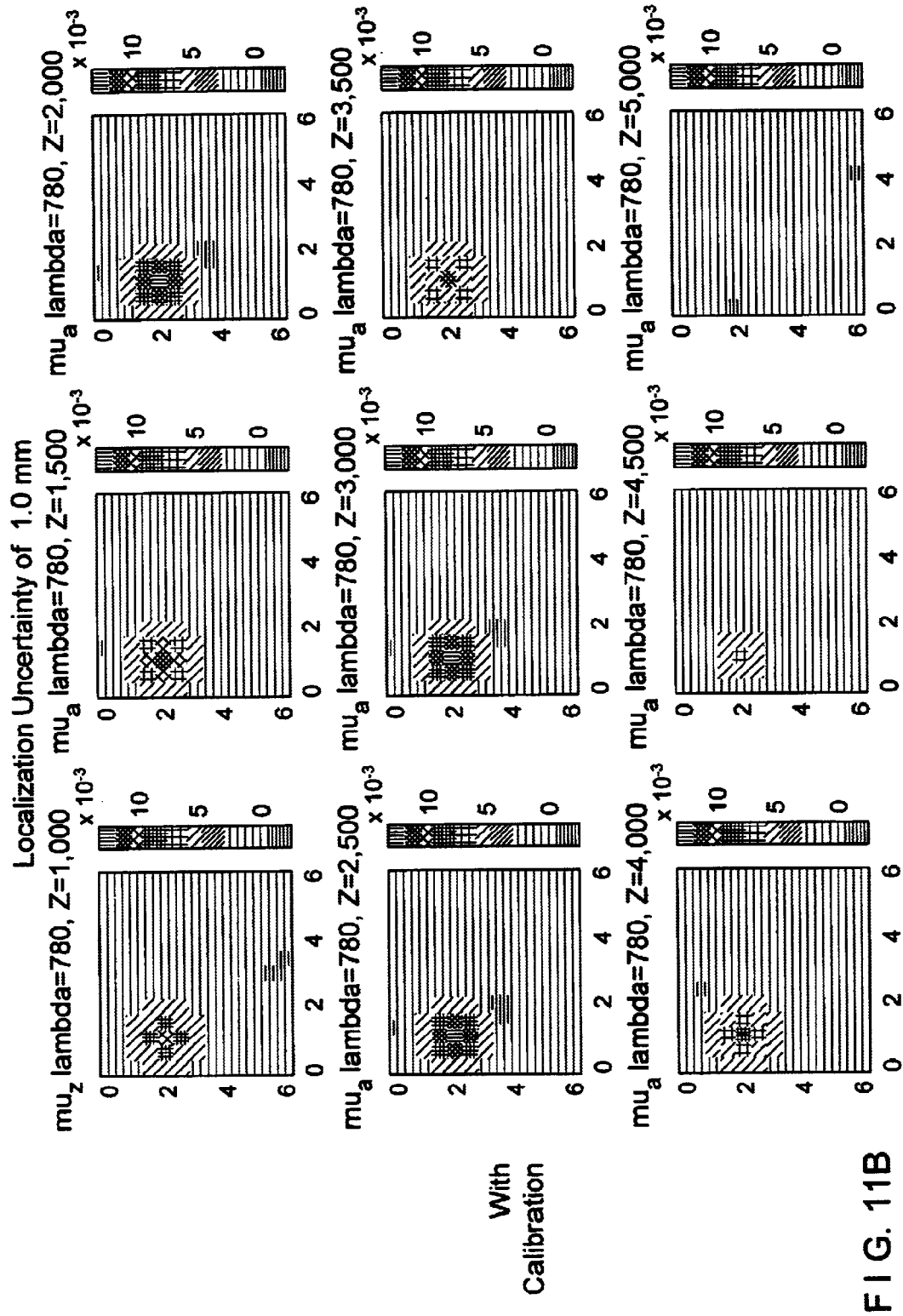
FIG. 11B is a set of images of simulated data obtained from the experimental geometry in FIG. 5, generated for localization uncertainty of e.g., 1.0 mm using a normalized Rytov approximation and including the reconstruction of freely varying source and detector location factors.

FIGS. 9A–11B illustrate the results obtained with the Rytov approximation excluding and including the reconstruction of the coupling coefficients for optode localization errors of 0.1, 0.5 and 1.0 mm, respectively. Referring to FIGS. 9A and 9B, the images of the simulated data obtained from the experimental geometry shown in FIG. 5 using a normalized Rytov approximation excluding and including the reconstruction of freely varying source and detector location factors, are illustrated for localization uncertainty of 0.1 mm. With the localization error of 0.1 mm, it is possible to locate the position of the absorbing heterogeneity despite the presence of image speckle near the top and bottom surfaces of the scattering medium.

With the localization errors of 0.5 mm and greater (See FIGS. 10A and 10B, and FIGS. 11A and 11B, the surface speckle noise obscures the presence of the absorbing heterogeneity. The speckle noise may arise directly from the localization error. In most, if not all, cases, including the calibration of optode location in the inverse problem significantly reduces the surface speckle noise revealing the absorbing object.

Example 2

Phantom Results

Figure 12:
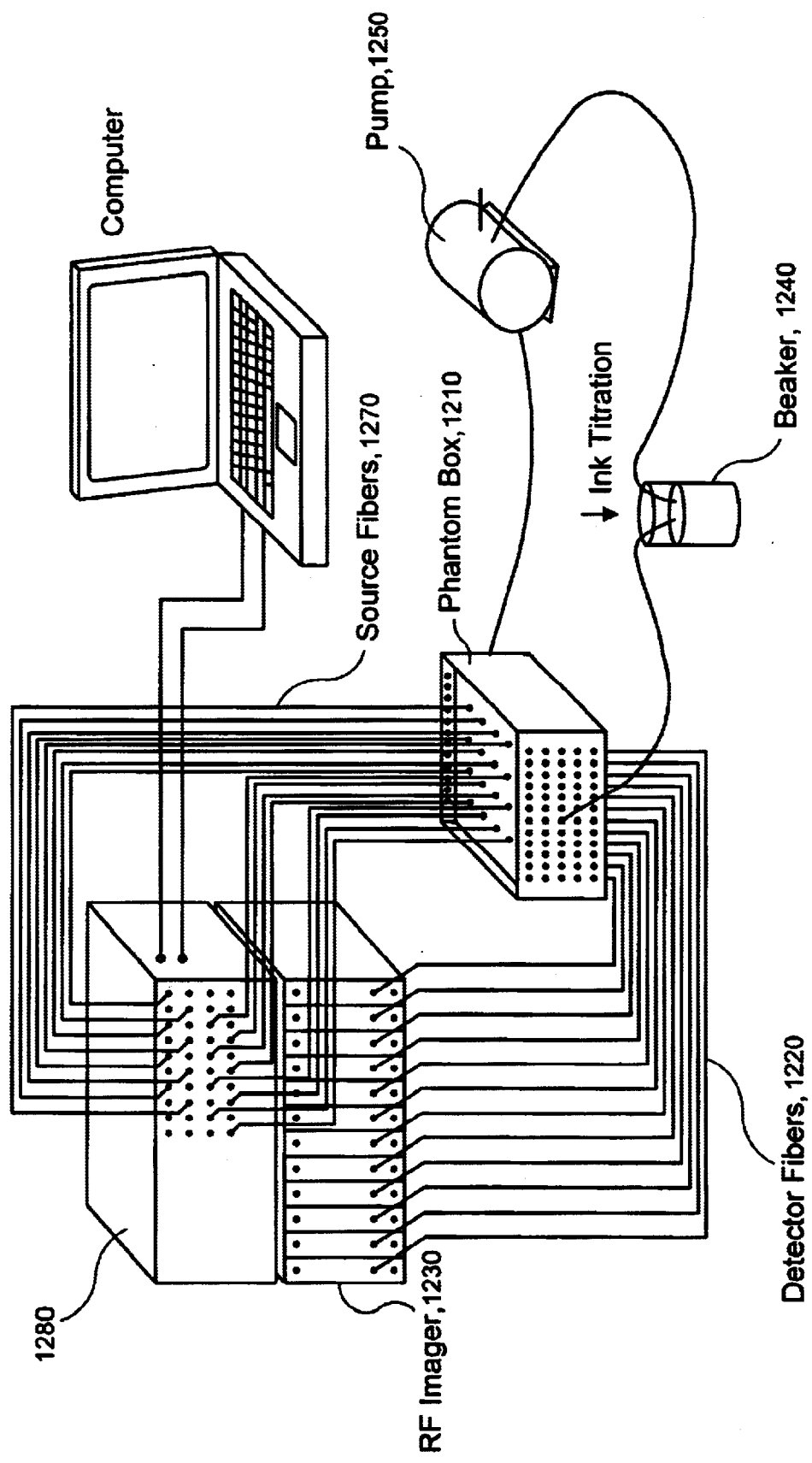
FIG. 12 is an example of the experimental setup of the system according to the present invention.

The actual image results of a phantom have also been obtained, and FIG. 12 shows the experimental setup for imaging the phantom. A phantom box 1210 has a set of sources and a set of detectors on its top and bottom plates, respectively. The phantom box 1210 is connected with an RF Imager 1230 with a set of detector fibers 1220. The phantom box 1210 is also connected with a controller 1280 via a set of source fibers 1270. A processing arrangement 1290 is coupled with the controller 1280. The phantom box 1210 is further coupled with a beaker 1240 and a pump 1250.

The phantom box 1210 was filled with 0.5% intralipid solution, and a 2-cm diameter heterogeneity sphere was embedded in this solution. The content of the sphere was controlled by the circulation channel outside the phantom box 1210, which included the pump 1250 and the beaker 1240 for ink titration. In the experiment, a slab geometry was formed, with the slab having a thickness of 5.11 cm. The center of the ball was located 2.35 cm from the bottom of the slab. There were sources on the top plate (z=0 cm) and detectors on the bottom plate (z=5.11 cm). The signal to the sources was delivered via the source fibers 1270. The signal was light with a wavelength of 830 nm and was modulated at 70 MHz. The amplitude and phase of the diffusely transmitted light were measured. Data was collected from the detectors via the detector fibers 1220 into the radio frequency imager 1230. The processing arrangement 1290 processed the results and generated the images.

Figure 13A:
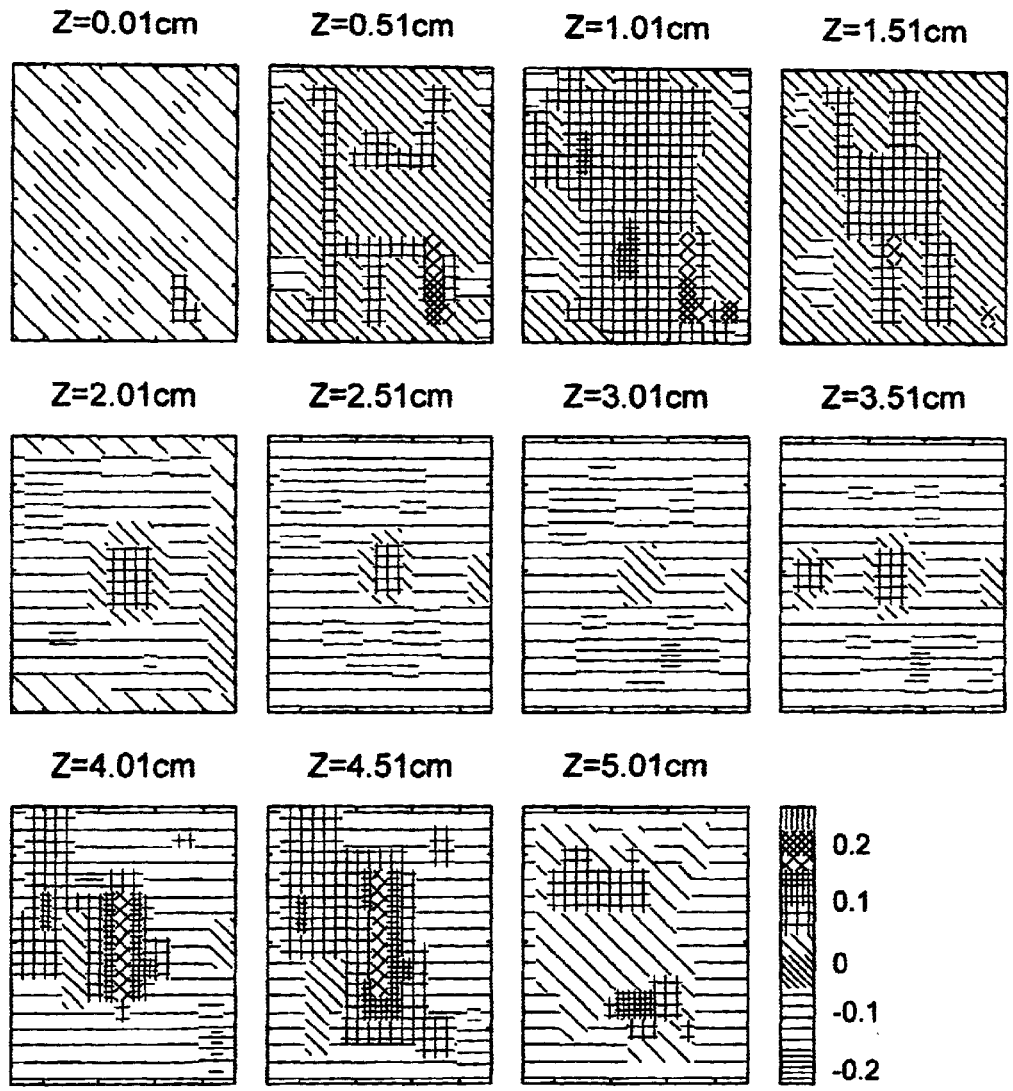
FIG. 13A is a set of images of data obtained from the experiment of FIGS. 9A and 9B using a normalized Rytov approximation excluding the reconstruction of freely varying source and detector calibration factors.
Figure 13B:
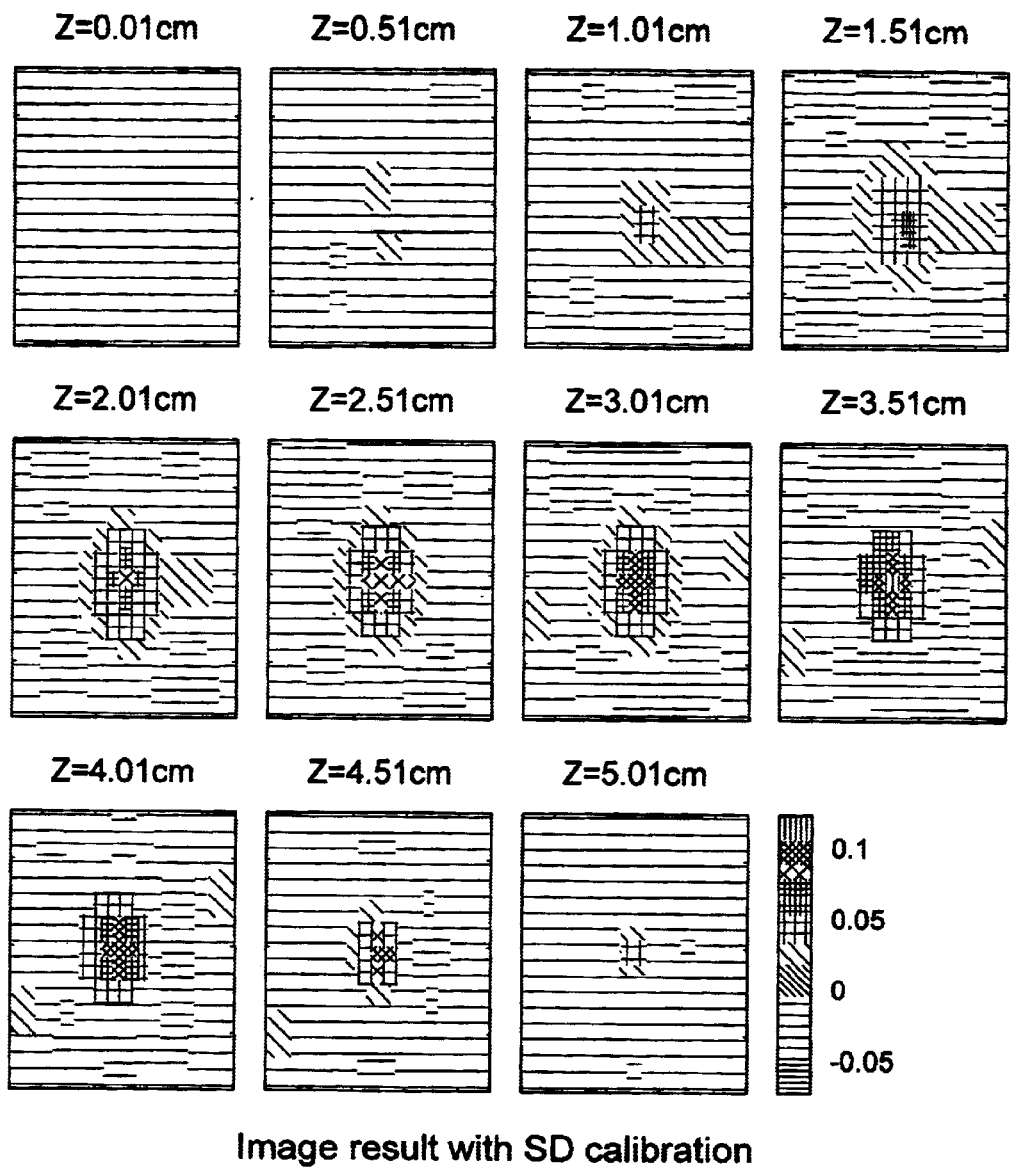
FIG. 13B is a set of images of data obtained from the experiment of FIGS. 9A and 9B using a normalized Rytov approximation including the reconstruction of freely varying source and detector calibration factors.

The images were first generated using the Rytov approximation both excluding and including the reconstruction of the source and detector coupling factors. Images were median filtered using standard techniques because this was found effective in removing speckle artifacts. FIG. 13A shows the images obtained excluding the reconstruction of the source and detector coupling factors, and FIG. 13B shows the images generated including the reconstruction. The X and Y ranges are in centimeters, and Z-slices are vertically arranged from 0.01 (top left) to 5.501 cm (bottom right) in 0.50-cm steps. It is observed that including reconstruction of the source and detector coupling factors improves image quality. In particular, the detail of the heterogeneity sphere can be seen in FIG. 13B for Z=2.01 to Z=3.51 cm, but it may not be observable over the corresponding Z-range in FIG. 13A.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a distribution of one or more properties in a medium illuminated with radiation from one or more sources, the method comprising the steps of:
    a. receiving the radiation exiting the medium;
    b. deriving one or more optical properties of the medium using one or more calibration factors and the radiation received in step (a), wherein the calibration factors are variables; and
    c. determining the distribution in the medium using the one or more optical properties derived in step (b), wherein each of the optical properties is utilized to obtain at least one of the following to determine the distribution:
        amplitude and phase of the radiation exiting the medium, and
        intensity and temporal delay of the radiation exiting the medium.

2. The method of claim 1, wherein at least one of the calibration factors is a source coupling factor.

3. The method of claim 1, wherein at least one of the calibration factors is a detector coupling factor.

4. The method of claim 1, wherein at least one of the calibration factors is a source location factor.

5. The method of claim 1, wherein at least one of the calibration factors is a detector location factor.

6. The method of claim 1, wherein the medium has characteristics so as to highly scatter the radiation entering therein.

7. The method of claim 1, wherein the radiation is an electromagnetic radiation.

8. The method of claim 1, wherein the radiation is an infrared radiation.

9. The method of claim 1, wherein the radiation comprises near-infrared photons.

10. The method of claim 1, wherein the radiation is a continuous-wave radiation.

11. The method of claim 10, wherein at least one of the optical properties includes an absorption coefficient.

12. The method of claim 10, wherein at least one of the optical properties includes a scattering coefficient.

13. The method of claim 1, wherein the optical properties are spatially varying optical properties.

14. The method of claim 1, wherein each of the optical properties is utilized to obtain the amplitude and phase of the radiation exiting the medium.

15. The method of claim 1, wherein each of the optical properties is utilized to obtain the intensity and temporal delay of the radiation exiting the medium.

16. The method of claim 1, further comprising the step of:
    d. before step (b), obtaining one or more parameters of the radiation received in step (a).

17. The method of claim 16, wherein at least one of the parameters is fluence.

18. The method of claim 17, wherein the step (b) comprises the substep of solving an inverse problem based on the one or more parameters and the one or more optical properties.

19. The method of claim 16, wherein the obtained parameters are functions of the calibration factors.

20. The method of claim 19, wherein at least one of the calibration factors is a source coupling factor.

21. The method of claim 19, wherein at least one of the calibration factors is a detector coupling factor.

22. The method of claim 19, wherein at least one of the calibration factors is a source location factor.

23. The method of claim 19, wherein at least one of the calibration factors is a detector location factor.

24. The method of claim 1, wherein at least one of the one or more optical properties includes an absorption coefficient value.

25. The method of claim 1, wherein at least one of the one or more optical properties includes a scattering coefficient value.

26. The method of claim 1, wherein the one or more optical properties include an absorption coefficient and a scattering coefficient.

27. The method of claim 1, further comprising the step of:
    e. reconstructing at least one image of the medium by using the distribution determined in step (c).

28. The method of claim 27, further comprising the step of:
    f. displaying the reconstructed images for review by human operators.

29. A method of determining a distribution of one or more properties in a medium illuminated with radiation from one or more sources, the method comprising the steps of:
    a. receiving the radiation exiting the medium;
    b. deriving one or more optical properties of the medium using one or more calibration factors and the radiation received in step (a), wherein the calibration factors are variables, and wherein step (b) comprises the substep of solving an inverse problem based on the one or more parameters and the one or more optical properties; and
    c. determining the distribution in the medium using the one or more optical properties derived in step (b)

d. before step (b), obtaining one or more parameters of the radiation received in step (a), wherein at least one of the parameters is fluence, wherein the solving substep comprises the substep of minimizing the equation:

$$F(x) = \sum_{i=1}^{N_{meas}} [\ln\Phi_{Theory,i}(x) - \ln\Phi_{Meas,i}]^2,$$

wherein index $N_{max}$ is a number of measurements of the received radiation,
$M_{Theory(x)}$ is a theoretical fluence,
$M_{Meas(x)}$ is a measured fluence, and
x is a vector providing a value of a property distribution for each voxel representing a portion of the medium.

30. The method of claim 29, wherein the minimizing substep comprises utilizing a linear approximation.

31. The method of claim 30, wherein the linear approximation is a Rytov approximation.

32. The method of claim 30, wherein the linear approximation is a Born approximation.

33. A method of measuring a distribution of at least one property within a medium, the method comprising:
    a. illuminating the medium with radiation from a plurality of sources;
    b. receiving radiation from the medium with a plurality of detectors;
    c. measuring at least one parameter of the received radiation; and
    d. calculating the distribution of the at least one property based on the at least one measured parameter by including source and detector calibration factors as freely varying quantities that are reconstructed in a model for a radiative transport within the medium.

34. The method of claim 33, wherein a probability that photons entering the medium will scatter greatly exceeds a probability that the photons entering the medium will be absorbed.

35. The method of claim 33, wherein the radiation is an electromagnetic radiation.

36. The method of claim 33, wherein the radiation is a continuous-wave radiation.

37. The method of claim 33, wherein the radiation is an infrared radiation.

38. The method of claim 33, wherein each source is spatially separated from each detector.

39. The method of claim 33, wherein the measured parameters are at least one absorption parameter and at least one scattering parameter.

40. The method of claim 33, wherein the measured parameters are at least one amplitude parameter and at least one phase parameter.

41. The method of claim 33, wherein the measured parameters are at least one amplitude parameter and at least one temporal off-set parameter.

42. The method of claim 33, wherein the property distribution is a distribution of at least one of absorption coefficient values and scattering coefficient values.

43. The method of claim 33, further comprising the step of
    e. displaying the property distribution in at least one image.

44. The method of claim 33, wherein the model includes a non-linear dependence on at least one measured parameter.

45. The method of claim 33, wherein the model includes a linear dependence on at least one measured parameter.

46. The method of claim 33, wherein the model includes a Rytov approximation.

47. The method of claim 46, wherein the model includes the substep of minimizing the following equation:

$$F(x) = \sum_{i=1}^{N_{meas}} [\ln\Phi_{Theory,i}(x) - \ln\Phi_{Meas,i}]^2,$$

wherein
$N_{max}$ is a number of measurements of the received radiation,
$M_{Theory(x)}$ is a theoretical fluence,
$M_{Meas(x)}$ is a measured fluence, and
x is a vector providing a value of the property distribution for each voxel of at least one image.

48. The method of claim 33, wherein the model includes an arrangement for scaling all measured parameters taken as input to make the measured parameters dimensionless and to be of the same order as the source and detector calibration factors.

49. A computer readable medium, comprising:
    a program, which when executed, is capable of causing a processor to:
    (i) receive radiation exiting the medium,
    (ii) derive one or more optical properties of the medium by using the received radiation and one or calibration factors, wherein the calibration factors are variables, and
    (iii) determine as output the distribution of one or more optical properties based on the received radiation and one or more calibration factors,
    wherein each of the optical properties is utilized to obtain at least one of the following to determine the distribution:
        amplitude and phase of the radiation exiting the medium, and
        intensity and temporal delay of the radiation exiting the medium.

50. The computer readable medium of claim 49, wherein the program, when executed, is capable of causing the processor to reconstruct at least one image of the output.

51. The computer readable medium of claim 49, wherein at least one of the calibration factors is a source coupling factor.

52. The computer readable medium of claim 49, wherein at least one of the calibration factors is a detector coupling factor.

53. The computer readable medium of claim 49, wherein at least one of the calibration factors is a source location factor.

54. The computer readable medium of claim 49, wherein at least one of the calibration factors is a detector location factor.

55. The computer readable medium of claim 49, wherein the medium has characteristics so as to highly scatter light entering therein.

56. The computer readable medium of claim 49, wherein the optical properties are spatially varying optical properties.

57. The computer readable medium of claim 49, wherein the program causes the processor to obtain one or more parameters of the radiation exiting the medium.

58. The computer readable medium of claim 57, wherein at least one of the one or more parameters is fluence.

59. The computer readable medium of claim 58, wherein the program, when executed, is capable of causing the processor to solve an inverse problem based on the one or more parameters and the one or more optical properties.

60. A computer readable medium, comprising:
a program, which when executed, is capable of causing a processor to:
(i) receive radiation exiting the medium,
(ii) derive one or more optical properties of the medium by using the received radiation and one or calibration factors, wherein the calibration factors are variables, and
(iii) determine as output the distribution of one or more optical properties based on the received radiation and one or more calibration factors,
wherein the program causes the processor to obtain one or more parameters of the radiation exiting the medium, at least one of the parameters being fluence,
wherein the program, when executed, is capable of causing the processor to solve an inverse problem based on the one or more parameters and the one or more optical properties, and
wherein the program, when executed, is capable of causing the processor to minimize the equation:

$$F(x) = \sum_{i=1}^{N_{meas}} [\ln\Phi_{Theory,i}(x) - \ln\Phi_{Meas,i}]^2,$$

wherein
$N_{max}$ is a number of measurements of the received radiation,
$M_{Theory(x)}$ is a theoretical fluence,
$M_{Meas(x)}$ is a measured fluence, and
x is a vector providing a value of the property distribution for each voxel of at least one image.

61. The computer readable medium of claim 60, wherein the program, when executed, is capable of causing the processor to utilize a linear approximation for minimizing the equation F(x).

62. The computer readable medium of claim 61, wherein the linear approximation is a Born approximation.

63. The computer readable medium of claim 61, wherein the linear approximation is a Rytov approximation.

64. The computer readable medium of claim 63, wherein the obtained parameters of radiation exiting the medium are functions of the calibration factors.

65. A computer readable medium comprising:
a program, which, when executed, is capable of causing a processor to:
(i) obtain at least one measured parameter of radiation exiting a medium,
(ii) calculate a distribution of at least one property based on the at least one measured parameter by including calibration factors as freely varying quantities that are reconstructed in a model for radiative transport within the medium, and
(iii) provide the property distribution as output.

66. The system of claim 65, wherein at least one of the calibration factors is a source coupling factor.

67. The system of claim 65, wherein at least one of the calibration factors is a detector coupling factor.

68. The system of claim 65, wherein at least one of the calibration factors is a source location factor.

69. The system of claim 65, wherein at least one of the calibration factors is a detector location factor.

70. The computer readable medium of claim 65, wherein the model includes a non-linear dependence on at least one measured parameter.

71. The computer readable medium of claim 65, wherein the model includes a linear dependence on at least one measured parameter.

72. The computer readable medium of claim 65, wherein the model includes a Rytov approximation.

73. The computer readable medium of claim 65, wherein the program, when executed, is capable of causing the processor to minimize the equation:

$$F(x) = \sum_{i=1}^{N_{meas}} [\ln\Phi_{Theory,i}(x) - \ln\Phi_{Meas,i}]^2,$$

wherein:
$N_{max}$ is a number of measurements of the received radiation,
$M_{Theory(x)}$ is a theoretical fluence,
$M_{Meas(x)}$ is a measured fluence, and
x is a vector providing a value of the property distribution for each voxel of at least one image.

74. The computer readable medium of claim 73, wherein the model includes scaling all measured parameters taken as input to make the measured parameters dimensionless and of the same order as the source and detector calibration factors.

75. A system for determining a distribution of one or more optical properties of a medium illuminated with radiation from one or more sources, comprising:
a. one or more detectors for receiving radiation; and
b. a processor coupled to the one or more detectors for deriving one or more optical properties from the radiation and one or more calibration factors, wherein the calibration factors are variables, wherein the processor is programmed to determine the distribution from the derived optical properties, and wherein each of the optical properties is utilized to obtain at least one of the following to determine the distribution:
amplitude and phase of the radiation exiting the medium, and
intensity and temporal delay of the radiation exiting the medium.

76. The system of claim 75, further comprising:
c. a computer database, operationally coupled to the processor, for storing a program that causes the processor to derive the optical properties and determine the distribution.

77. The system of claim 76, wherein at least one of the calibration factors is a source coupling factor.

78. The system of claim 76, wherein at least one of the calibration factors is a detector coupling factor.

79. The system of claim 76, wherein at least one of the calibration factors is a source location factor.

80. The system of claim 76, wherein at least one of the calibration factors is a detector location factor.

81. The system of claim 76, wherein the medium has characteristics so as to highly scatter radiation entering therein.

82. The system of claim 76, wherein the optical properties are spatially varying optical properties.

83. The system of claim 76, wherein the radiation is an electromagnetic radiation.

84. The system of claim 76, wherein the radiation is an infrared radiation.

85. The system of claim 76, wherein the radiation comprises near-infrared photons.

86. The system of claim 76, wherein the radiation is a continuous-wave radiation.

87. The system of claim 86, wherein at least one of the optical properties includes an absorption coefficient.

88. The system of claim 86, wherein at least one of the optical properties includes a scattering coefficient.

89. The system of claim 75, wherein each of the optical properties is utilized to obtain the amplitude and phase of the radiation exiting the medium.

90. The system of claim 75, wherein each of the optical properties is utilized to obtain the intensity and temporal delay of the radiation exiting the medium.

91. The system of claim 76, wherein the one or more detectors are adapted to obtain one or more parameters of the radiation.

92. The system of claim 91, wherein at least one of the parameters is fluence.

93. The system of claim 92, wherein the processor is programmed to solve an inverse problem based on the one or more parameters and the one or more optical properties.

94. The system of claim 76, wherein at least one of the one or more optical properties includes an absorption coefficient.

95. The system of claim 76, wherein at least one of the one or more optical properties includes a scattering coefficient.

96. The system of claim 76, wherein the one or more optical properties include both absorption and scattering coefficients.

97. The system of claim 76, wherein the processor is programmed to reconstruct at least one image of the medium by using the determined distribution.

98. The system of claim 97, wherein the processor is programmed to display the reconstructed images for review by human operators.

99. A system for determining a distribution of one or more optical properties of a medium illuminated with radiation from one or more sources, comprising:

a. one or more detectors for receiving radiation; and b. a processor coupled to the one or more detectors for deriving one or more optical properties from the radiation and one or more calibration factors, wherein the calibration factors are variables, and wherein the processor is programmed to determine the distribution from the derived optical properties, wherein the one or more detectors are adapted to obtain one or more parameters of the radiation, at least one of the parameters being fluence, wherein the processor is programmed to solve an inverse problem based on the one or more parameters and the one or more optical properties, and wherein the processor is programmed to minimize the equation:

$$F(x) = \sum_{i=1}^{N_{meas}} [\ln\Phi_{Theory,i}(x) - \ln\Phi_{Meas,i}]^2,$$

wherein:

$N_{max}$ is a number of measurements of the received radiation, $M_{Theory(x)}$ is a theoretical fluence, $M_{Meas(x)}$ is a measured fluence, and x is a vector providing a value of the property distribution for each voxel of at least one image.

100. The system of claim 99, wherein the processor is programmed to utilize a linear approximation.

101. The system of claim 100, wherein the linear approximation is a Born approximation.

102. The system of claim 100, wherein the linear approximation is a Rytov approximation.

103. The system of claim 102, wherein the obtained parameters are functions of the calibration factors.

104. The system of claim 103, wherein at least one of the calibration factors is a source coupling factor.

105. The system of claim 103, wherein at least one of the calibration factors is a detector coupling factor.

106. The system of claim 103, wherein at least one of the calibration factors is a source location factor.

107. The system of claim 103, wherein at least one of the calibration factors is a detector location factor.

108. A system for measuring a property distribution within a medium, the system comprising:

a. a plurality of radiation sources;

b. a plurality of detectors that convert the radiation received into signals; and c. a processor that processes the signals to provide values of the distribution of at least one property of the medium, wherein the values are obtained by applying a model for radiative transport in the medium that reconstructs calibration factors using freely varying quantities.

109. The system of claim 108, wherein at least one of the calibration factors is a source coupling factor.

110. The system of claim 108, wherein at least one of the calibration factors is a detector coupling factor.

111. The system of claim 108, wherein at least one of the calibration factors is a source location factor.

112. The system of claim 108, wherein at least one of the calibration factors is a detector location factor.

113. The system of claim 108, wherein each source comprises an optical fiber and a laser, and wherein each detector comprises an optical fiber and a photodetector.

114. The system of claim 108, wherein the radiation is an electromagnetic radiation.

115. The system of claim 108, wherein the radiation is a continuous-wave radiation.

116. The system of claim 108, wherein the radiation is an infrared radiation.

117. The system of claim 108, wherein each source is spatially separated from each detector.

118. The system of claim 117, wherein each source extends in a first plane and each detector extends in a second plane which is opposite to the first plane.

119. The system of claim 118, wherein each source is spatially separated from the other sources by about 2 centimeters and each detector is spatially separated from the other detectors by about 2 centimeters.

120. The system of claim 108, wherein the processor provides output of at least one of absorption values and scattering values.

121. The system of claim 108, further comprising a display to provide an image of at least one property of the medium.

122. The system of claim 121, wherein the display is a computer screen.

123. The system of claim 108, wherein the model is non-linear.

124. The system of claim 108, wherein the model is linear.

125. The system of claim 108, wherein the model includes a Rytov approximation.

126. The system of claim 125, wherein the model includes minimizing $$F(x) = \sum_{i=1}^{N_{meas}} [\ln \Phi_{Theory,i}(x) - \ln \Phi_{Meas,i}]^2,$$

wherein:
$N_{max}$ is a number of measurements of the received radiation,
$M_{Theory(x)}$ is a theoretical fluence,
$M_{Meas(x)}$ is a measured fluence, and
x is a vector providing a value of the property distribution for each voxel of at least one image.

127. The system of claim 126, wherein the model includes scaling parameters extracted from the signal as input to make them dimensionless and of the same order as the source and detector calibration factors.

128. A software system which, when executed on a processing device, determines a distribution of one or more optical properties in a medium illuminated with radiation from one or more sources, the software system comprising:
 a processing subsystem which, when executed on the processing device, configures the processing device to perform the following:
 a. obtains parameters of the radiation exiting the medium,
 b. derives one or more optical properties of the medium using one or more calibration factors and the obtained parameters, wherein the calibration factors are variables, and
 c. determines the distribution in the medium using the one or more derived optical properties,
 wherein each of the optical properties is utilized to obtain at least one of the following to determine the distribution:
  amplitude and phase of the radiation exiting the medium, and
  intensity and temporal delay of the radiation exiting the medium.

129. The software system of claim 128, wherein at least one of the calibration factors is a source coupling factor.

130. The software system of claim 128, wherein at least one of the calibration factors is a detector coupling factor.

131. The software system of claim 128, wherein at least one of the calibration factors is a source location factor.

132. The software system of claim 128, wherein at least one of the calibration factors is a detector location factor.

133. A system for determining a distribution of one or more optical properties of a medium illuminated with radiation from one or more sources, comprising:
 a. means for receiving radiation exiting the medium;
 b. means for deriving one or more optical properties of the medium using one or more calibration factors and the received radiation, wherein the calibration factors are variables; and
 d. means for determining the distribution in the medium using the derived optical properties,
 wherein each of the optical properties is utilized to obtain at least one of the following to determine the distribution:
  amplitude and phase of the radiation exiting the medium, and
  intensity and temporal delay of the radiation exiting the medium.

134. The system of claim 133, wherein at least one of the calibration factors is a source coupling factor.

135. The system of claim 133, wherein at least one of the calibration factors is a detector coupling factor.

136. The system of claim 133, wherein at least one of the calibration factors is a source location factor.

137. The system of claim 133, wherein at least one of the calibration factors is a detector location factor.

* * * * *

UNITED STATES PATENT AND TRADEMARK OFFICE
CERTIFICATE OF CORRECTION

PATENT NO. : 6,956,650 B2 Page 1 of 1
APPLICATION NO. : 10/045309
DATED : October 18, 2005
INVENTOR(S) : Boas et al.

It is certified that error appears in the above-identified patent and that said Letters Patent is hereby corrected as shown below:

|  | Reads | Should Read |
|---|---|---|
| In the Specification | | |
| Col. 2, Line 19 | "to minimize" | -- To minimize -- |
| Col. 4, Line 45 | "in still" | -- In still -- |
| Col. 8, Line 50 | " $\dfrac{v\delta\mu_a}{D_o}G(r,r_d)dr,$ " | -- $\dfrac{v\delta\mu_a(r)}{D_o}G(r,r_d)dr,$ -- |
| Col. 11, Line 47 | "resealing" | -- rescaling -- |
| Col. 11, Line 51 | "form, For" | -- form. For -- |
| Col. 12, Line 29 | "location si substantially" | -- location is substantially -- |
| Col. 12, Line 56 | "location si substantially" | -- location is substantially -- |

Signed and Sealed this

Fifth Day of February, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,956,650 B2 | Page 1 of 1 |
| APPLICATION NO. | : 10/045309 | |
| DATED | : October 18, 2005 | |
| INVENTOR(S) | : David A. Boas et al. | |

It is certified that error appears in the above-identified patent and that said Letters Patent is hereby corrected as shown below:

In the Specification

Col. 1 lines 11-18

Please replace paragraph under the "Statement As To Federally Sponsored Research" section with the following paragraph as follows:

STATEMENT AS TO FEDERALLY SPONSORED RESEARCH

This invention was made with Government support under Grant Numbers NS038842 and RR014075 awarded by the National Institutes of Health and DAMD17-99-2-9001 awarded by the U.S. Army. The Government has certain rights in this invention.

Signed and Sealed this
Twenty-second Day of September, 2015

Michelle K. Lee
*Director of the United States Patent and Trademark Office*